United States Patent [19]

Ciechanover et al.

[11] Patent Number: 5,384,255

[45] Date of Patent: Jan. 24, 1995

[54] UBIQUITIN CARRIER ENZYME E2-F1, PURIFICATION, PRODUCTION, AND USE

[75] Inventors: Aaron J. Ciechanover; Nava Blumenfeld; Hedva Gonen, all of Haifa, Israel

[73] Assignee: Rappaport Family Institute for Research in the Medical Sciences, Haifa, Israel

[21] Appl. No.: 80,073

[22] Filed: Jun. 21, 1993

[51] Int. Cl.$^6$ ............... C12N 9/10; C12N 15/54
[52] U.S. Cl. ................................ 435/193; 435/7.4; 435/172.3; 435/252.3; 435/240.2; 435/320.1; 435/172.1; 536/23.2
[58] Field of Search ............... 425/193, 172.3, 320.1; 536/23.2

[56] References Cited

PUBLICATIONS

Ciechanover et al., Ubiquitin Dependence of Selective Protein Degradation Demonstrated in the Mammalian Cell Cycle Mutant ts85, *Cell* 37:57–66 (May 1984).
Ciechanover et al., ATP-dependent conjugation of reticulocyte proteins with the polypeptide required for protein degradation, *Proc. Natl. Acad. Sci. USA* 77(3):1365–1368 (Mar. 1980).
Ciechanover et al., "Covalent Affinity" Purification of Ubiquitin-activating Enzyme, *Journal of Biological Chemistry* 257(5):2537–2542 (Mar. 10, 1982).
Dohmen et al., The N-end rule is mediated by the UBC2(RAD6) ubiquitin-conjugating enzyme, *Proc. Natl. Acad. Sci. USA* 88:7351–7355 (Aug. 1991).
Donehower et al., Mice deficient for p53 are developmentally normal but susceptible to spontaneous tumours, *Nature* 35:215–221 (Mar. 19, 1992).
Girod et al., A Major Ubiquitin Conjugation System in Wheat Germ Extracts Involves a 15-kDa Ubiquitin–conjugating Enzyme (E2) Homologous to the Yeast UBC4/UBC5 Gene Products, *J. Biol. Chem.* 268:955–960 Jan. 15, 1993.
Goebl et al., The Yeast Cell Cycle Gene CDC34 Encodes a Ubiquitin-Conjugating Enzyme, *Science* 241:1331–1335 (Sep. 9, 1988).
Gonen et al., Purification and Characterization of a Novel Protein That Is Required for Degradation of N-α-Acetylated Proteins by the Ubiquitin System, *J. of Biol. Chem.* 266:19221–19231 (Oct. 15, 1991).
Heller et al., A Ubiquitin-Protein Ligase Specific for Type III Protein Substrates, *Journal of Biological Chemistry* 265(12):6532–6535 (Apr. 25, 1990).
Hershko et al., Components of Ubiquitin-Protein Ligase System, *Journal of Biological Chemistry* 258(13):8206–8214 (Jul. 10, 1983).
Hershko et al., Resolution of the ATP-dependent proteolytic system from reticulocytes: A Component that interacts with ATP, *Proc. Natl. Acad. Sci. USA* 76(7):3107–3110 (Jul. 1979).
Hershko et al., The Ubiquitin System For Protein Degradation, *Annu. Rev. Biochem.* 61:761–807 (1992).
Hingamp et al., A ubiqutin conjugating enzyme encoded by African swine fever virus, *The EMBO Journal* 11(1):361–366 (1992).

(List continued on next page.)

Primary Examiner—Robert A. Wax
Assistant Examiner—Rebecca Prouty
Attorney, Agent, or Firm—Sterne, Kessler Goldstein & Fox

[57] ABSTRACT

A method for isolating and purifying novel species of E2 ubiquitin-carrier protein, designated E2-F1, is disclosed. A method for preparing enzymatically active fragments of E2-F1 enzyme is also disclosed. The use of purified E2-F1 to produce antibodies is also disclosed. The use of such E2-F1-specific antibodies to detect the presence of E2-F1 in a biological sample, and to inhibit protein degradation are also disclosed. Recombinant DNA molecules which code for E2-F1, and recombinant hosts and vectors which contain E2-F1 coding sequences are also disclosed. The use of such recombinant hosts and vectors to produce E2-F1 protein is also disclosed. The use of purified E2-F1 to identify and to isolate E3 enzyme is also disclosed. Methods for screening substances for the ability to inhibit E2-F1 enzyme activity are also disclosed.

1 Claim, 4 Drawing Sheets

PUBLICATIONS

Jentsch et al., The Yeast DNA repair gene RAD6 encodes a ubiquitin-conjugating enzyme, *Nature* 329:131-134 (Sep. 10, 1987).

Liu et al., cDNA Cloning of a Novel Human Ubiquitin Carrier Protein, *Journal of Biological Chemistry* 267(22):15829-15835 (Aug. 5, 1992).

Mayer et al., Degradation of Proteins with Acetylated Amino Termini by the Ubiquitin System, *Science* 244:1480-1483 (Jun. 23, 1989).

Pickart et al., Functional Heterogeneity of Ubiquitin Carrier Proteins, *Journal of Biological Chemistry* 260(3):1573-1581 (Feb. 10, 1985).

Reiss et al., Specificity of Binding of $NH_2$-terminal Residue of Proteins to Ubiquitin-Protein Ligase, Use of Amino Acid Derivatives To Characterize Specific Binding Sites, *J. Biol. Chem.* 263(6):2693-2698 (Feb. 25, 1988).

Reiss et al., Affinity Purification of Ubiquitin-Protein Ligase on Immobilized Protein Substrates, Evidence for The Existence of Separate $NH_2$-Terminal Bindings Sites On A Single Enzyme, *Journal of Biological Chemistry* 265:3685-3690 (Mar. 5, 1990).

Reiss et al., Binding Sites of Ubiquitin-Protein Ligase, Binding of Ubiquitin-Protein Conjugates And Of Ubiquitin-Carrier Protein, *Journal of Biological Chemistry* 264(18):10378-10383 (Jun. 25, 1989).

Scheffner et al., The E6 Oncoprotein Encoded by Human Papillomavirus Types 16 and 18 Promotes the Degradation of p53, *Cell* 63:1129-1136 (Dec. 21, 1990).

Seufert et al., Ubiquitin-conjugating enzymes UBC4 and UBC5 mediate selective degradation of short-lived and abnormal proteins, *The EMBO Journal* 9(2):543-550 (1990).

Seufert et al., UBC1 encodes a novel member of an essential subfamily of yeast ubiquitin-conjugating enzymes involved in protein degradation, *The EMBO Journal* 9(13):4535-4541 (1990).

Sullivan et al., Cloning of a 16-kDa Ubiquitin Carrier Protein from Wheat and *Arabidopsis thaliana*, Identification Of Functional Domains By In Vitro Mutagenesis, *J. Biol. Chem.* 266(35):23878-23885 (Dec. 15, 1991).

Sullivan et al., A ubiquitin carrier protein from wheat germ is structurally and functionally similar to the yeast DNA repair enzyme encoded by *RAD6*, *Proc. Natl. Acad. Sci. USA* 86:9861-9865 (Dec. 1989).

Sung et al., Yeast *RAD6* encoded ubiquitin conjugating enzyme mediates protein degradation dependent on the N-end-recognizing E3 enzyme, *The EMBO Journal* 10(8):2187-2193 (1991).

Treier et al., *Drosphila UbcD1* encodes a highly conserved ubiquitin-conjugating enzyme involved in selective protein degradation, *The EMBO Journal* 11(1):367-372 (1992).

Werness et al., Association of Human Papillomavirus Types 16 and 18 E6 Proteins with p53, *Science* 248:76-79 (Apr. 6, 1990).

Wing et al., A Rabbit Reticulocyte Ubiquitin Carrier Protein That Supports Ubiquitin-dependent Proteolysis ($E2_{14k}$) Is Homologous to the Yeast DNA Repair Gene RAD6, *Journal of Biological Chemistry* 267(10):6495-6501 (Apr. 5, 1992).

FRAGMENT 7:

| | | | |
|---|---|---|---|
| E2-F1 R Retic: | ?- I Y H P N I D E K -? | (100) |
| E2-14 R Musc: | 76- M F H P N V Y A D -84 | (33) |
| UBC1 Sc: | 75- V Y H P N I S S V -83 | (56) |
| UBC2/RAD6 Sc: | 76- M F H P N V Y A N -84 | (33) |
| UBC3/cdc34 Sc: | 83- I Y H P N V Y R D -91 | (56) |
| UBC4 Sc: | 74- I Y H P N I N A N -82 | (67) |
| UBC5 Sc: | 74- I Y H P N I N S S -82 | (67) |
| UBCD1 Dm: | 73- I Y H P N I N S N -81 | (67) |
| E2 ASFV: | 78- I Y S D G K L C I -86 | (22) |
| E2-23 Tv: | 72- I Y H P N V D E M -80 | (78) |
| E2-16 At: | 76- M F H P N I Y A D -84 | (44) |

FRAGMENT 17:

| | | | |
|---|---|---|---|
| E2-F1 R Retic: | ?- I E I N F P A E Y P F K P P K -? | (100) |
| E2-14 R Musc: | 55- L V I E F S E E Y P N K P P T -96 | (53) |
| UBC1 Sc: | 54- V D I E V P M E Y P F K P P K -68 | (67) |
| UBC2/RAD6 Sc: | 55- L L L E F D E E Y P N K P P H -69 | (47) |
| UBC3/cdc34 Sc: | 62- A Q M R F P E D F P F S P P Q -76 | (33) |
| UBC4 Sc: | 53- L S I H F P T D Y P F K P P K -67 | (67) |
| UBC5 Sc: | 53- L S I H F P T D Y P F K P P K -67 | (67) |
| UBCD1 Dm: | 52- L T I H F P T D Y P F K P P K -66 | (67) |
| E2 ASFV: | 52- A K I V F P P K Y P Y E P P R -66 | (47) |
| E2-23 Tv: | 51- V R V E L T E A Y P Y K S P S -65 | (27) |
| E2-16 At: | 55- L S L Q F S E D Y P N K P P T -69 | (40) |

FRAGMENT 20:

| | | | |
|---|---|---|---|
| E2-F1 R Retic: | ?- T D Q V I Q S L I A L V N D P Q P E H P L R -? | (100) |
| E2-14 R Musc: | 102- V S S I L T S I Q S L L D E P N P N S P A N -123 | (23) |
| UBC1 Sc: | 102- L K S A L I S L Q A L L Q S P E P N D P Q D -123 | (32) |
| UBC2/RAD6 Sc: | 102- N A S I L T S I N S L F N D P N P A S P A N -123 | (32) |
| UBC3/cdc34 Sc: | 121- V E S V L I S I V S L L E D P N I N S P A N -123 | (27) |
| UBC4 Sc: | 100- L S K V L L S I C S L L T D A N P D D P L V -121 | (32) |
| UBC5 Sc: | 100- L S K V L L S I C S L L T D A N P D D P L V -121 | (32) |
| UBCD1 Dm: | 99- I S K V L L S I C S L L C D P N P D D P L V -120 | (36) |
| E2 ASFV: | 107- I D T V L L S V I S L L N E P N P D S P A N -128 | (41) |
| E2-23 Tv: | 102- V N I F E V F L P Q L L L Y P N P S D P L N -123 | (27) |
| E2-16 At: | 102- V A A I L T S I Q S L L C D P N P N S P A N -123 | (27) |

FIG.4

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
( A ) LENGTH: 25 amino acids (B) TYPE: amino acid
(D) TOPOLOGY: linear (xi) SEQUENCE DESCRIPTION: SEQ ID NO:1:

```
Xaa Xaa Phe Arg Asn Ile Gln Val Asp Xaa Ala Asn Leu Leu Thr Xaa
 1               5                  10                      15
Gln Gly Leu Ile Val Pro Asp Asn Pro
                20              25
```

(2) INFORMATION FOR SEQ ID NO:2:

(i) SEQUENCE CHARACTERISTICS:
(A) LENGTH: 19 amino acids
(B) TYPE: amino acid
(D) TOPOLOGY: linear (xi) SEQUENCE DESCRIPTION: SEQ ID NO:2:

```
Xaa Xaa Leu Glu His Pro Leu Lys Ala Xaa Thr Xaa Xaa Phe Tyr Asn
 1               5                  10                      15
Ile Xaa Val
```

(2) INFORMATION FOR SEQ ID NO:3:

(i) SEQUENCE CHARACTERISTICS:
(A) LENGTH: 9 amino acids
(B) TYPE: amino acid
(D) TOPOLOGY: linear (xi) SEQUENCE DESCRIPTION: SEQ ID NO:3:

```
Ile Tyr His Pro Asn Ile Asp Glu Lys
 1               5
```

(2) INFORMATION FOR SEQ ID NO:4:

(i) SEQUENCE CHARACTERISTICS:
(A) LENGTH: 15 amino acids
(B) TYPE: amino acid
(D) TOPOLOGY: linear (xi) SEQUENCE DESCRIPTION: SEQ ID NO:4:

```
Ile Glu Ile Asn Phe Pro Ala Glu Tyr Pro Phe Lys Pro Pro Lys
 1               5                  10                      15
```

(2) INFORMATION FOR SEQ ID NO:5:

(i) SEQUENCE CHARACTERISTICS:
(A) LENGTH: 22 amino acids
(B) TYPE: amino acid
(D) TOPOLOGY: linear (xi) SEQUENCE DESCRIPTION: SEQ ID NO:5:

```
Thr Asp Gln Val Ile Gln Ser Leu Ile Ala Leu Val Asn Asp Pro Gln
 1               5                  10                      15
Pro Glu His Pro Leu Arg
                20
```

(2) INFORMATION FOR SEQ ID NO:6:

(i) SEQUENCE CHARACTERISTICS:
(A) LENGTH: 5 amino acids
(B) TYPE: amino acid
(D) TOPOLOGY: linear (xi) SEQUENCE DESCRIPTION: SEQ ID NO:6:

```
Val Lys Val Gly Val
 1               5
```

(2) INFORMATION FOR SEQ ID NO:7:

(i) SEQUENCE CHARACTERISTICS:
    (A) LENGTH: 9 amino acids
    (B) TYPE: amino acid
    (D) TOPOLOGY: linear (xi) SEQUENCE DESCRIPTION: SEQ ID NO:7:

Ile Tyr His Pro Asn Ile Asp Glu Lys
    1               5

(2) INFORMATION FOR SEQ ID NO:8:

(i) SEQUENCE CHARACTERISTICS:
    (A) LENGTH: 9 amino acids
    (B) TYPE: amino acid
    (D) TOPOLOGY: linear (xi) SEQUENCE DESCRIPTION: SEQ ID NO:8:

Met Phe His Pro Asn Val Tyr Ala Asp
    1               5

(2) INFORMATION FOR SEQ ID NO:9:

(i) SEQUENCE CHARACTERISTICS:
    (A) LENGTH: 9 amino acids
    (B) TYPE: amino acid
    (D) TOPOLOGY: linear (xi) SEQUENCE DESCRIPTION: SEQ ID NO:9:

Val Tyr His Pro Asn Ile Ser Ser Val
    1               5

(2) INFORMATION FOR SEQ ID NO:10:

(i) SEQUENCE CHARACTERISTICS:
    (A) LENGTH: 9 amino acids
    (B) TYPE: amino acid
    (D) TOPOLOGY: linear (xi) SEQUENCE DESCRIPTION: SEQ ID NO:10:

Met Phe His Pro Asn Val Tyr Ala Asn
    1               5

(2) INFORMATION FOR SEQ ID NO:11:

(i) SEQUENCE CHARACTERISTICS:
    (A) LENGTH: 9 amino acids
    (B) TYPE: amino acid
    (D) TOPOLOGY: linear (xi) SEQUENCE DESCRIPTION: SEQ ID NO:11:

Ile Tyr His Pro Asn Val Tyr Arg Asp
    1               5

(2) INFORMATION FOR SEQ ID NO:12:

(i) SEQUENCE CHARACTERISTICS:
    (A) LENGTH: 9 amino acids
    (B) TYPE: amino acid
    (D) TOPOLOGY: linear (xi) SEQUENCE DESCRIPTION: SEQ ID NO:12:

Ile Tyr His Pro Asn Ile Asn Ala Asn
    1               5

(2) INFORMATION FOR SEQ ID NO:13:

(i) SEQUENCE CHARACTERISTICS:
    (A) LENGTH: 9 amino acids (B) TYPE: amino acid
(D) TOPOLOGY: linear (xi) SEQUENCE DESCRIPTION: SEQ ID NO:13:

Ile Tyr His Pro Asn Ile Asn Ser Ser
1               5

(2) INFORMATION FOR SEQ ID NO:14:

(i) SEQUENCE CHARACTERISTICS:
    (A) LENGTH: 9 amino acids
    (B) TYPE: amino acid
    (D) TOPOLOGY: linear (xi) SEQUENCE DESCRIPTION: SEQ ID NO:14:

Ile Tyr His Pro Asn Ile Asn Ser Asn
1               5

(2) INFORMATION FOR SEQ ID NO:15:

(i) SEQUENCE CHARACTERISTICS:
    (A) LENGTH: 9 amino acids
    (B) TYPE: amino acid
    (D) TOPOLOGY: linear (xi) SEQUENCE DESCRIPTION: SEQ ID NO:15:

Ile Tyr Ser Asp Gly Lys Leu Cys Ile
1               5

(2) INFORMATION FOR SEQ ID NO:16:

(i) SEQUENCE CHARACTERISTICS:
    (A) LENGTH: 9 amino acids
    (B) TYPE: amino acid
    (D) TOPOLOGY: linear (xi) SEQUENCE DESCRIPTION: SEQ ID NO:16:

Ile Tyr His Pro Asn Val Asp Glu Met
1               5

(2) INFORMATION FOR SEQ ID NO:17:

(i) SEQUENCE CHARACTERISTICS:
    (A) LENGTH: 9 amino acids
    (B) TYPE: amino acid
    (D) TOPOLOGY: linear (xi) SEQUENCE DESCRIPTION: SEQ ID NO:17:

Met Phe His Pro Asn Ile Tyr Ala Asp
1               5

(2) INFORMATION FOR SEQ ID NO:18:

(i) SEQUENCE CHARACTERISTICS:
    (A) LENGTH: 15 amino acids
    (B) TYPE: amino acid
    (D) TOPOLOGY: linear (xi) SEQUENCE DESCRIPTION: SEQ ID NO:18:

Ile Glu Ile Asn Phe Pro Ala Glu Tyr Pro Phe Lys Pro Pro Lys
1               5                   10                  15

(2) INFORMATION FOR SEQ ID NO:19:

(i) SEQUENCE CHARACTERISTICS:
    (A) LENGTH: 15 amino acids
    (B) TYPE: amino acid
    (D) TOPOLOGY: linear (xi) SEQUENCE DESCRIPTION: SEQ ID NO:19:

```
        Leu  Val  Ile  Glu  Phe  Ser  Glu  Glu  Tyr  Pro  Asn  Lys  Pro  Pro  Thr
        1              5                        10                         15
```

( 2 ) INFORMATION FOR SEQ ID NO:20:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:20:

```
        Val  Asp  Ile  Glu  Val  Pro  Met  Glu  Tyr  Pro  Phe  Lys  Pro  Pro  Lys
        1              5                        10                         15
```

( 2 ) INFORMATION FOR SEQ ID NO:21:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:21:

```
        Leu  Leu  Leu  Glu  Phe  Asp  Glu  Glu  Tyr  Pro  Asn  Lys  Pro  Pro  His
        1              5                        10                         15
```

( 2 ) INFORMATION FOR SEQ ID NO:22:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:22:

```
        Ala  Gln  Met  Arg  Phe  Pro  Glu  Asp  Phe  Pro  Phe  Ser  Pro  Pro  Gln
        1              5                        10                         15
```

( 2 ) INFORMATION FOR SEQ ID NO:23:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:23:

```
        Leu  Ser  Ile  His  Phe  Pro  Thr  Asp  Tyr  Pro  Phe  Lys  Pro  Pro  Lys
        1              5                        10                         15
```

( 2 ) INFORMATION FOR SEQ ID NO:24:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:24:

```
        Leu  Thr  Ile  His  Phe  Pro  Thr  Asp  Tyr  Pro  Phe  Lys  Pro  Pro  Lys
        1              5                        10                         15
```

( 2 ) INFORMATION FOR SEQ ID NO:25:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:25:

```
        Ala  Lys  Ile  Val  Phe  Pro  Pro  Lys  Tyr  Pro  Tyr  Glu  Pro  Pro  Arg
        1              5                        10                         15
```

( 2 ) INFORMATION FOR SEQ ID NO:26:

( i ) SEQUENCE CHARACTERISTICS:
     ( A ) LENGTH: 15 amino acids
     ( B ) TYPE: amino acid
     ( D ) TOPOLOGY: linear ( x i ) SEQUENCE DESCRIPTION: SEQ ID NO:26:

```
Val  Arg  Val  Glu  Leu  Thr  Glu  Ala  Tyr  Pro  Tyr  Lys  Ser  Pro  Ser
1                   5                        10                       15
```

( 2 ) INFORMATION FOR SEQ ID NO:27:

( i ) SEQUENCE CHARACTERISTICS:
     ( A ) LENGTH: 15 amino acids
     ( B ) TYPE: amino acid
     ( D ) TOPOLOGY: linear ( x i ) SEQUENCE DESCRIPTION: SEQ ID NO:27:

```
Leu  Ser  Leu  Gln  Phe  Ser  Glu  Asp  Tyr  Pro  Asn  Lys  Pro  Pro  Thr
1                   5                        10                       15
```

( 2 ) INFORMATION FOR SEQ ID NO:28:

( i ) SEQUENCE CHARACTERISTICS:
     ( A ) LENGTH: 22 amino acids
     ( B ) TYPE: amino acid
     ( D ) TOPOLOGY: linear ( x i ) SEQUENCE DESCRIPTION: SEQ ID NO:28:

```
Thr  Asp  Gln  Val  Ile  Gln  Ser  Leu  Ile  Ala  Leu  Val  Asn  Asp  Pro  Gln
1                   5                        10                       15

Pro  Glu  His  Pro  Leu  Arg
                20
```

( 2 ) INFORMATION FOR SEQ ID NO:29:

( i ) SEQUENCE CHARACTERISTICS:
     ( A ) LENGTH: 22 amino acids
     ( B ) TYPE: amino acid
     ( D ) TOPOLOGY: linear ( x i ) SEQUENCE DESCRIPTION: SEQ ID NO:29:

```
Val  Ser  Ser  Ile  Leu  Thr  Ser  Ile  Gln  Ser  Leu  Leu  Asp  Glu  Pro  Asn
1                   5                        10                       15

Pro  Asn  Ser  Pro  Ala  Asn
                20
```

( 2 ) INFORMATION FOR SEQ ID NO:30:

( i ) SEQUENCE CHARACTERISTICS:
     ( A ) LENGTH: 22 amino acids
     ( B ) TYPE: amino acid
     ( D ) TOPOLOGY: linear ( x i ) SEQUENCE DESCRIPTION: SEQ ID NO:30:

```
Leu  Lys  Ser  Ala  Leu  Ile  Ser  Leu  Gln  Ala  Leu  Leu  Gln  Ser  Pro  Glu
1                   5                        10                       15

Pro  Asn  Asp  Pro  Gln  Asp
                20
```

( 2 ) INFORMATION FOR SEQ ID NO:31:

( i ) SEQUENCE CHARACTERISTICS:
     ( A ) LENGTH: 22 amino acids
     ( B ) TYPE: amino acid
     ( D ) TOPOLOGY: linear ( x i ) SEQUENCE DESCRIPTION: SEQ ID NO:31:

Val Ala Ser Ile Leu Thr Ser Ile Asn Ser Leu Phe Asn Asp Pro Asn
1               5                   10                  15

Pro Ala Ser Pro Ala Asn
            20

( 2 ) INFORMATION FOR SEQ ID NO:32:

( i ) SEQUENCE CHARACTERISTICS:
( A ) LENGTH: 22 amino acids
( B ) TYPE: amino acid
( D ) TOPOLOGY: linear ( x i ) SEQUENCE DESCRIPTION: SEQ ID NO:32:

Val Glu Ser Val Leu Ile Ser Ile Val Ser Leu Leu Glu Asp Pro Asn
1               5                   10                  15

Ile Asn Ser Pro Ala Asn
            20

( 2 ) INFORMATION FOR SEQ ID NO:33:

( i ) SEQUENCE CHARACTERISTICS:
( A ) LENGTH: 22 amino acids
( B ) TYPE: amino acid
( D ) TOPOLOGY: linear ( x i ) SEQUENCE DESCRIPTION: SEQ ID NO:33:

Leu Ser Lys Val Leu Leu Ser Ile Cys Ser Leu Leu Thr Asp Ala Asn
1               5                   10                  15

Pro Asp Asp Pro Leu Val
            20

( 2 ) INFORMATION FOR SEQ ID NO:34:

( i ) SEQUENCE CHARACTERISTICS:
( A ) LENGTH: 22 amino acids
( B ) TYPE: amino acid
( D ) TOPOLOGY: linear ( x i ) SEQUENCE DESCRIPTION: SEQ ID NO:34:

Ile Ser Lys Val Leu Leu Ser Ile Cys Ser Leu Leu Cys Asp Pro Asn
1               5                   10                  15

Pro Asp Asp Pro Leu Val
            20

( 2 ) INFORMATION FOR SEQ ID NO:35:

( i ) SEQUENCE CHARACTERISTICS:
( A ) LENGTH: 22 amino acids
( B ) TYPE: amino acid
( D ) TOPOLOGY: linear ( x i ) SEQUENCE DESCRIPTION: SEQ ID NO:35:

Ile Asp Thr Val Leu Leu Ser Val Ile Ser Leu Leu Asn Glu Pro Asn
1               5                   10                  15

Pro Asp Ser Pro Ala Asn
            20

( 2 ) INFORMATION FOR SEQ ID NO:36:

( i ) SEQUENCE CHARACTERISTICS:
( A ) LENGTH: 22 amino acids
( B ) TYPE: amino acid
( D ) TOPOLOGY: linear ( x i ) SEQUENCE DESCRIPTION: SEQ ID NO:36:

-continued

Val Asn Ile Phe Glu Val Phe Leu Pro Gln Leu Leu Leu Tyr Pro Asn
1               5               10                      15

Pro Ser Asp Pro Leu Asn
            20

( 2 ) INFORMATION FOR SEQ ID NO:37:

( i ) SEQUENCE CHARACTERISTICS:
        ( A ) LENGTH: 22 amino acids
        ( B ) TYPE: amino acid
        ( D ) TOPOLOGY: linear ( x i ) SEQUENCE DESCRIPTION: SEQ ID NO:37:

Val Ala Ala Ile Leu Thr Ser Ile Gln Ser Leu Leu Cys Asp Pro Asn
1               5               10                      15

Pro Asn Ser Pro Ala Asn
            20

UBIQUITIN CARRIER ENZYME E2-F1, PURIFICATION, PRODUCTION, AND USE

BACKGROUND OF THE INVENTION

Part of the work performed during development of this invention utilized U.S. Government funds. Therefore, the U.S. Government has certain rights in this invention.

1. Field of the Invention

This invention is directed to a novel species of E2 ubiquitin-carrier protein of eukaryotes. In particular, this invention is directed to E2-F1, which is isolated and purified from rabbit reticulocytes. This invention is further directed to the use of purified E2-F1 to produce antibodies, and the use of such antibodies to detect the presence of E2-F1 in a biological sample. This invention is also directed to the use of E2-F1 antibodies to inhibit protein degradation. This invention is further directed to recombinant DNA molecules which code liar E2-F1, and to recombinant hosts and vectors which contain the gene coding for E2-F1. This invention is also directed to the use of such recombinant hosts and vectors to produce E2-F1 protein. This invention is further directed to the use of purified E2-F1 to identity and isolate E3 enzyme. This invention is also directed to methods for screening substances for the ability to inhibit E2-F1 enzyme activity.

2. Related Art a. Ubiquitin-Mediated Protein Degradation

Intracellular protein degradation plays an important role in the regulation of the levels of specific proteins and the elimination of damaged, or abnormal proteins (for recent reviews, see Hershko et al., *Annu. Rev. Biochem.* 61:761–807 (1992); Jentsch, *Annu. Rev. Genet.* 26:179–207 (1992)). This process is highly selective in that certain proteins are degraded in minutes, while other proteins are practically stable. In general, regulatory proteins or enzymes have fast turnover rates, so that their levels can be rapidly changed in response to appropriate stimuli. In some cases, the rates of degradation of regulatory proteins are controlled with great precision. For example, cyclin levels oscillate at certain stages of the cell cycle and thus, control cell cycle progression.

It is necessary to identify and to characterize enzymatic reactions involved in intracellular protein degradation in order to understand mechanisms which underlie the selectivity and regulation of intracellular protein breakdown. It now appears that the selective degradation of many proteins in eukaryotic cells is carried out by the ubiquitin-mediated pathway. Ubiquitination of proteins has been implicated in a variety of key cellular processes such as the regulation of cell cycle and division, removal of detective proteins, provision of amino acids under stressed conditions, presentation of antigens, degradation of oncoproteins and tumor suppressors, the heat shock response, DNA repair, and the modification of histones and receptors. Moreover, the pathological alteration of ubiquitin-mediated protein degradation may contribute to the pathogenesis of certain neurodegenerative diseases, as well as severe muscle wasting in bedridden patients.

Ubiquitin-mediated protein degradation is a multistep process. Briefly, ligation of ubiquitin is initiated by the activation of its C-terminal Gly residue, which is catalyzed by a specific ubiquitin-activating enzyme, E1. This step consists of the intermediary formation of ubiquitin adenylate (with the displacement of PPi from ATP), and the transfer of activated ubiquitin to a thiol site of E1 (with the subsequent release of AMP). Next, activated ubiquitin is transferred by transacylation to thiol groups of a family of ubiquitin-carrier proteins, E2(s). E2-ubiquitin thiol esters are the donors of ubiquitin for isopeptide bond formation between the C-terminal Gly residue of ubiquitin and ε-amino groups of Lys residues of proteins. Ubiquitin-protein ligation may occur by direct transfer from E2, or by a process in which target proteins are first bound to specific sites of ubiquitin-protein ligases, E3(s), and then ubiquitin is transferred from E2. Proteins which are ligated to multiple ubiquitin units are degraded by a 26S protease complex.

Much attention has been directed to understanding the specific structural features of proteins that are recognized by the ubiquitin system. The first type of recognition signal that was elucidated was the amino acid residue at the N-terminal position. The 20 different amino acid residues have been classified into "stabilizing" or "destabilizing" with respect to the half-lives they conferred on a model protein (i.e., β-galactosidase) when they were introduced into the N-terminal position of the protein (Bachmair et al., *Science* 234:179–186 (1986)). The resulting rule, designated the "N-end rule," proposes that the in vivo half-life of a protein is a function of its amino-terminal residue (Bachmair et al., supra; Bachmair et al., *Cell* 56:1019–1032 (1989)). As discussed below, more recent evidence indicates that the bulk of proteins degraded by the ubiquitin system are recognized by signals that are distinct from the N-terminal residue.

b. Components of the Ubiquitin System

Elucidation of the three-step mechanism involved in ubiquitin conjugate formation was greatly facilitated by the development of "covalent" affinity chromatography of crude reticulocyte extracts over immobilized ubiquitin. The method takes advantage of the mechanism of activation of ubiquitin in which the first enzyme in the pathway, the ubiquitin-activating enzyme, E1, generates a thiol ester with ubiquitin in the presence of ATP. Part of the bound E1 is exchanged via transthiolation with E2s to yield immobilized E2-ubiquitin thiol ester. Following elution of E1 with AMP and PPi (that reverse the E1-dependent activation reaction), purified E2s are recovered following elution with dithiothreitol (Ciechanover, A. et al., *J. Biol. Chem.* 257:2537–2542 (1982); Hershko, A. et al., *J. Biol. Chem.* 258:8206–8214 (1983)).

Two species of ubiquitin-protein ligases, E3s, have been purified and characterized. One enzyme, E3α, binds noncovalently to ubiquitin via recognition of complementary structural motifs (Hershko, A. et al., *J. Biol. Chem.* 258:8206–8214 (1983)). This ligase recognizes mostly proteins with basic (Arg, His, Lys) and bulky-hydrophobic (Leu, Phe, Trp, Tyr) free N-terminal residues (Reiss, Y. et al., *J. Biol. Chem.* 263:2693–2698 (1988); Reiss, Y. et al., *J. Biol. Chem.* 265:3685–3690 (1990); Reiss, Y. et al., *J. Biol. Chem.* 264:10378–10383 (1989)). The second ligase characterized, E3β, recognizes proteins with small uncharged residues (such as Ala, Ser, and Thr) at their N-terminal residue (Heller, H. et al., *J. Biol. Chem.* 265:6532–6535 (1990)), though penultimate amino acid residues also contribute to the recognition (H. Heller and A. Hershko, unpublished results).

Studies in many organisms have shown that ubiquitin can be transferred from E1 to several species of E2s. Pickart and Rose described five different E2 enzymes in rabbit reticulocytes with molecular masses ranging from 14 to 32 kDa (Pickart, C. M. et at., *J. Biol. Chem.* 260:1573-1581 (1985)). All the enzymes are contained in Fraction 2. Ten species of E2s have been described in the yeast *Saccharomyces cerevisiae* (UBC1-10) and their corresponding genes cloned and sequenced (Jentsch, S., *Annu. Rev. Genet.* 26:179-207 (1992)).

Structurally, all known E2s share a conserved domain of approximately 16 kDa. This domain contains the Cys residue required for the formation of ubiquitin-E2 thiol ester. Certain E2 enzymes contain additional typical domains. Based on their structure, the E2 enzymes can be divided into three groups (Jentsch, S., *Annu. Rev. Genet.* 26:179-207 (1992)). Class I E2s consist almost exclusively of the conserved domain. Class II proteins have C-terminal extensions that may contribute to substrate recognition or to cellular localization. For example, yeast UBC2 and UBC3 have a highly acidic C-terminal domain that promote interaction with basic substrates such as histones (Jentsch, S., *Annu. Rev. Genet.* 26:179-207 (1992)). Class III enzymes have various N-terminal extensions, however, their function is not known.

Functional studies of E2 enzymes have shown that they can be clustered in two major groups. Most E2 enzymes catalyze transfer of ubiquitin to small amines or small basic proteins, such as histories or cytochrome C, in a reaction that does not require E3. The reactions catalyzed by these enzymes result in monoubiquitin derivatives that do not serve as proteolysis intermediates. Although the cellular roles of these enzymes are not known, genetic studies indicate that some of these E2s play important roles in a variety of basic cellular processes. For example, UBC3/CDC34 is essential for viability. Mutations in this E2 affect G1-S cell cycle progression, DNA replication, and spindle pole body separation. The enzyme interacts with CDC4 and CDC53 and appears to exert some of its effects via this interaction (Jentsch, S., *Annu. Rev. Genet.* 26:179-207 (1992); Goebl, M. et al., *Science* 241:1331-1335 (1988); Goebl, M. G. et al., *Trends Biochem. Sci.* 16:173-177 (1991)). UBC10/PAS2 is essential for peroxisome biogenesis (Jentsch, S., *Annu. Rev. Genet.* 26:179-207 (1992)). The roles of other species of monoubiquitinating E2s are not known. For example,disruption of UBC8 does not yield any detectable mutant phenotype (Jentsch, S., *Annu. Rev. Genet.* 26:179-207 (1992)).

The second major group of E2 enzymes is involved in multiple ubiquitination that targets the protein substrate for degradation. The mechanism of this reaction is quite different from that involved in monoubiquitination: here, the first activated ubiquitin moiety is transferred from E2 to a specific Lys residue of the substrate that is bound to E3 (Hershko, A. et al., *J. Biol. Chem.* 258:8206-8214 (1983); Hershko, A. et al., *Annu. Rev. Biochem.* 61:761-807 (1992)). In successive reactions, a polyubiquitin chain is synthesized by progressive transfer of activated ubiquitin moieties to Lys$^{48}$ of the previous (and already conjugated) ubiquitin molecule (Chau, V. et al., *Science* 243:1576-1583 (1989)). In some other cases, E2 and E3 mediate conjugation of single ubiquitin moieties to multiple Lys residues of the protein substrate (Hershko, A. et al., *Biochem. Biophys. Res. Commun.* 128:1079-1086 (1985)). During the entire reaction, the substrate remains bound to E3. The binding of the substrate to E3 probably facilitates the synthesis of the polyubiquitin chain (or the multiple single ubiquitinations). These chains (or the multiple ubiquitin moieties) serve, most likely, as recognition markers for the 26S protease that degrades these complexes: monoubiquitinated proteins are not recognized by the protease.

It is assumed that the E2 enzymes involved in proteolysis recognize distinct species of E3s. However, it is not known whether they also have specific recognition sites for the substrates. This task is accomplished, most probably, by the different ligases. Of the five E2s isolated originally from reticulocytes, only the 14 kDa enzyme was shown to be involved in E3-dependent multiple ubiquitination and subsequent degradation (Pickart, C. M. et al., *J. Biol. Chem.* 260:1573-1581 (1985)). Initial analysis of the mechanism of action of E3α revealed that in addition to the specific binding sites for ubiquitin and the substrate, it also interacts with one (or more) of the E2 enzymes with which it acts in concert (Reiss, Y. et al., *J. Biol. Chem.* 265:3685-3690 (1990); Reiss, Y. et al., *J. Biol. Chem.* 264:10378-10383 (1989)).

The formation of an E2-E3 complex probably facilitates the transfer of activated ubiquitin from E2 to the protein substrate bound to the ligase. Successive studies have shown that the ability of UBC3 (RAD6) to promote polyubiquitination and degradation in vitro is dependent upon the presence of E3α (Sung, P. et al., *EMBO J.* 10:2187-2193 (1991)). A similar study carried out in yeast demonstrated that UBC2 is physically associated with UBR1, the yeast homolog of E3α that recognizes certain proteins via their free N-terminal residues; immunoprecipitation of UBR1 also precipitated UBC2 (Jürgen Dohmem, R. et al., *Proc. Natl. Acad. Sci. USA* 88:7351-7355 (1991)). In addition, certain UBR1 substrates ("N-end rule" substrates; Varshavsky, A., *Cell* 69:725-735 (1992)) such as Arg-βgal and Leu-βgal were dramatically stabilized in UBC2 null mutants (Jürgen Dohmem, R. et al., *Proc. Natl. Acad. Sci. USA* 88:7351-7355 (1991); Varshavsky, A., *Cell* 69:725-735 (1992)).

Whereas many mechanistic aspects of the "N-end rule" have been elucidated, accumulating experimental evidence indicates that its physiological functions are rather limited, and the bulk of cellular proteins are recognized by signals that are distinct from the N-terminal residue (Hershko, A. et al., *Annu. Rev. Biochem.* 61:761-807 (1992)). For example, approximately 80% of the cellular proteins are N-α-acetylated (Brown, J. L. et al., *J. Biol. Chem.* 251:1009-1014 (1976)) and the majority of the residual unblocked proteins lack "destabilizing" N-terminal residues (Hershko, A. et al., *Annu. Rev. Biochem.* 61:761-807 (1992)). N-α-acetylated proteins can be degraded by the ubiquitin system, and removal of the blocking group is probably not necessary for recognition and degradation to occur (Mayer, A. et al., *Science* 244: 1480-1483 (1989)). Reiss and colleagues have shown directly that recognition of certain free N-terminal proteins is not dependent on the identity of their N-terminal amino acid residue (Reiss, Y. et al., *J. Biol. Chem.* 263:2693-2698 (1988)). Most convincing, mutational inactivation of the "N-end" pathway in yeast is neither lethal, nor phenotypically conspicuous (Bartel, B. et al., *EMBO J.* 9:3179-3189 (1990)).

Thus, if the notion that different E2 enzymes interact with specific ligases is true, a reasonable conclusion is that the "N-end" pathway E2s (the yeast UBC2 and the mammalian E2-14kDa) do not play an important role in ubiquitin-mediated proteolysis. Therefore, other, yet unidentified species of E2(s) probably account for targeting of most cellular proteins for degradation. One such E2 has been recently purified and characterized from wheat germ (Girod, P.-A. et al., *J. Biol. Chem.* 268:955–960 (1993)).

The present invention is directed to a novel species of a mammalian E2 that is involved in the conjugation and degradation of non N-end rule proteins.

SUMMARY OF THE INVENTION

The present invention is directed to isolated E2-F1 enzyme which is substantially pure, wherein the E2-F1 enzyme does not bind to anion exchange resin in neutral pH, and wherein the E2-F1 enzyme is capable of stimulating protein degradation of non N-end rule substrates and N-α-acetylated substrates. In addition, the present invention is directed to E2-F1 enzyme comprising the amino acid sequences of SEQ ID NO:3, SEQ ID NO:4 and SEQ ID NO:5. The present invention is also directed to enzymatically active fragments of the E2-F1 enzyme.

The present invention is also directed to a method of isolating and purifying E2-F1 enzyme from a biological sample, comprising the steps of:

(a) obtaining a crude lysate from a biological sample;
(b) fractionating the crude lysate with an anion exchange resin at neutral pH;
(c) collecting the unadsorbed fraction of the fractionated crude lysate of step (b) to obtain crude E2-F1 enzyme;
(d) subjecting the crude E2-F1 enzyme from step (c) to at least one gel filtration chromatography step to obtain E2-F1 enzyme preparation; and
(e) subjecting the E2-F1 enzyme preparation from step (d) to ion-exchange chromatography to obtain substantially pure E2-F1 enzyme.

The present invention is further directed to an antibody which is capable of binding specifically to E2-F1 enzyme. In particular, the invention is directed to E2-F1 enzyme-specific monoclonal antibodies, as well as to hybridoma cell lines which produce such monoclonal antibodies.

The present invention is further directed to a method of using isolated and purified E2-F1 enzyme to prepare monoclonal antibodies, comprising the steps of:

(a) immunizing mice with the E2-F1 enzyme;
(b) removing B-lymphocytes from the immunized mice;
(c) fusing the B-lymphocytes with myeloma cells, thereby producing hybridomas;
(d) cloning tile hybridomas;
(e) selecting positive clones which produce anti-E2-F1 enzyme antibody;
(f) culturing the anti-E2-F1 enzyme antibody-producing clones; and
(g) isolating anti-E2-F1 enzyme antibodies from the cultures.

The present invention is also directed to a method of using isolated and purified E2-F1 enzyme to prepare polyclonal antibodies in an animal, comprising the steps of:

(a) administering the E2-F1 enzyme to the animal; and
(b) isolating the polyclonal antibodies from the animal.

The present invention is also directed to a method of using the E2-F1 enzyme-specific antibody to detect the presence of E2-F1 enzyme in a biological sample, comprising the steps of:

(a) contacting the biological sample with at least one antibody capable of binding to tile E2-F1 enzyme; and
(b) detecting any of the antibody bound to E2-F1 enzyme.

The present invention is further directed to a purified and isolated DNA molecule coding for E2-F1 enzyme. The invention is also directed to an expression vector comprising such a E2-F1 enzyme coding DNA molecule.

The present invention is also directed to prokaryotic and eukaryotic hosts transformed with such an expression vector.

The present invention is further directed to a method of using expression vectors which comprise E2-F1 enzyme coding sequences to prepare E2-F1, comprising the steps of:

(a) introducing the expression vector into a host cell to produce a recombinant host cell;
(b) culturing the recombinant host cell; and
(c) isolating E2-F1 enzyme from the recombinant host cell.

The present invention is also directed to a method of producing E2-F1 enzyme, comprising the steps of:

(a) culturing a recombinant host comprising a gene coding for the E2-F1 enzyme; and
(b) isolating E2-F1 enzyme from the recombinant host.

The present invention is further directed to a method for inhibiting the degradation of proteins in cultured cells, comprising introducing an expression vector which comprises E2-F1 enzyme coding sequences into the cultured cells.

The present invention is also directed to a method of using the E2-F1 enzyme to detect the presence of E3 protein ligase in a biological sample, comprising the steps of:

(a) contacting the biological sample with the E2-F1 enzyme; and
(b) detecting any of E2-F1 enzyme bound to E3.

The present invention is also directed to a method for determining whether a substance is an inhibitor of E2-F1 enzyme activity, comprising the steps of:

(a) incubating the substance with E2-F1, E1, ATP, ubiquitin, a source of E3 ligase, and a substrate protein, whereby tile incubation promotes the conjugation of ubiquitin with the protein substrate;
(b) detecting ubiquitin-protein conjugates; and
(c) comparing the amount of ubiquitin-protein conjugate formed in the presence of the substance with the amount of ubiquitin-protein conjugate formed in the absence of the substance;

wherein a decrease in the amount of ubiquitin-protein conjugate formation in the presence of the substance indicates that inhibition of E2-F1 enzyme activity by the substance has occurred.

The present invention is further directed to a rapid screening method for determining whether a substance is an inhibitor of E2-F1 enzyme activity, comprising the steps of:

(a) incubating tile substance with cultured cells under conditions appropriate for entry of the substance into the cultured cells, wherein the cultured cells produce at least one identified protein which is degraded by an E2-F1-dependent pathway in the cultured cells;
(b) detecting the presence of the identified protein within the cultured cells; and
(c) comparing the amount of the identified protein from the cultured cells incubated in the presence of the substance with the amount of the identified protein from the cultured cells incubated in the absence of tile substance;

wherein an increase in the amount of the identified protein in the cultured cells incubated in the presence of the substance indicates that inhibition of the E2-F1 enzyme activity by the substance has occurred.

The present invention is also directed to a method of determining whether a substance is an inhibitor of E2-F1 enzyme activity in muscle tissue, comprising the steps of:

(a) incubating the substance with muscle tissue under conditions appropriate for promoting the degradation of ubiquitinated proteins;

(b) measuring the release of a product of muscle protein degradation by the muscle tissue; and (c) comparing the amount of the product of muscle protein degradation from muscle tissue incubated in the presence of the substance with the amount of the product of muscle protein degradation from muscle tissue incubated in the absence of the substance;

wherein an increase in the amount of the product of muscle protein degradation from muscle tissue in the presence of the substance indicates that inhibition of the E2-F1 enzyme activity by the substance has occurred.

The present invention is also directed to a method of determining whether a substance is an inhibitor of E2-F1 enzyme activity in an animal, comprising the steps of:

(a) administering the substance to the animal;

(b) measuring an indicator of protein degradation from the animal;

(c) comparing the amount of the indicator of protein degradation from the animal administered with the substance with the amount of the indicator of protein degradation from an animal which has not been administered the substance;

wherein an increase in the amount of the indicator of protein degradation from the animal administered with the substance indicates that inhibition of the E2-F1 enzyme activity by the substance has occurred.

The present invention is further directed to a method of inhibiting the loss of muscle mass in an animal, comprising administering an inhibitor of E2-F1 enzyme activity.

The present invention is also directed to a method of inhibiting the proliferation of cancer cells in an animal, comprising administering an inhibitor of E2-F1 enzyme activity to the animal, wherein the administration results in the entry of the inhibitor into the cancer cells. 3-methylhistidine.

BRIEF DESCRIPTION OF THE DRAWINGS

FIG. 4 shows an amino acid sequence comparison between E2-F1 from rabbit reticulocytes and several members of the ubiquitin-carrier protein family. Three internal tryptic peptides from purified E2-F1 rabbit reticulocytes (R Relic) were generated, sequenced, and compared with related proteins as described under Example 4. The proteins used for comparison were: the 14 kDa E2 from rabbit muscle (E2-14 R Musc), the E2 UBC1 from the yeast *Saccharomyces cerevisiae* (Ubc1 Sc), the E2 UBC2/RAD6 from the yeast *Saccharomyces cerevisiae* (UBC2/RAD6 Sc), the E2 UBC3/cdc34 from the yeast *Saccharomyces cerevisiae* (UBC3/cdc34 Sc), the E2 proteins UBC4 and UBC5 from the yeast *Saccharomyces cerevisiae* (UBC4 Sc and UBC5 Sc), E2 UBCD1 from the fruit fly *Drosophila melanogaster* (UBCD1 Din), E2 from the African Swine Fever Virus (E2, ASFV), the 23 kDa E2 from the wheat germ *Triticum vulgate* (E2-23 Tv), and the 16 kDa E2 from the high plant *Arabidopsis thaliana* (E2-16 At). Identical amino acid residues are indicated by shaded boxes. Numbers flanking the sequences indicate positions of residues along the polypeptide chain, whereas numbers in brackets indicate homology in percentage.

DEFINITIONS

Figure 1:
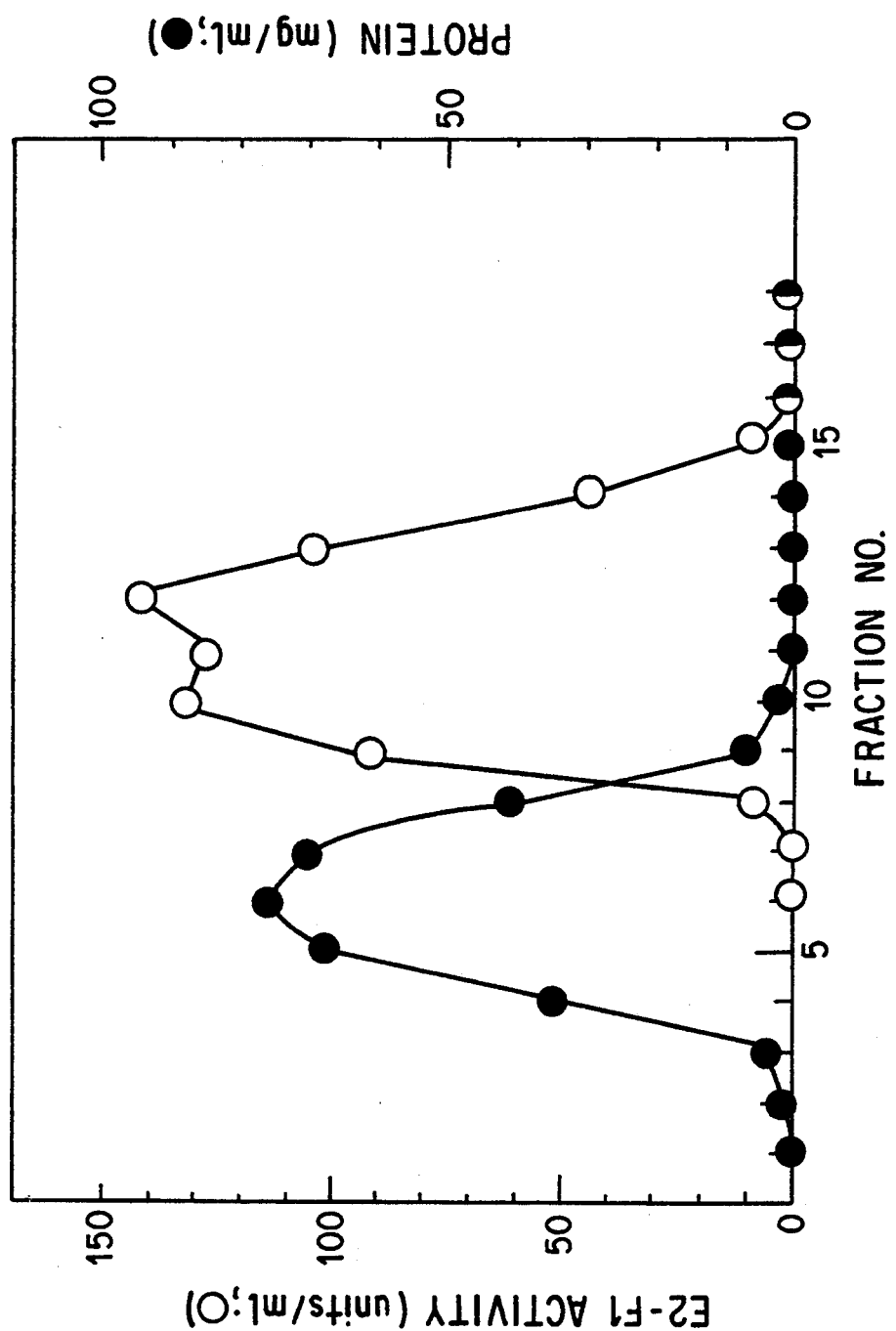
FIG. 1 shows tile separation of crude reticulocyte Fraction 1 on a Sephadex G-50 column. Fraction numbers refer to fractions collected following disposal of the first 550 ml of the elution buffer. Closed circles denote protein concentration and open circles denote activity.

In the description that follows, a number of terms used in recombinant DNA technology are utilized extensively. In order to provide a clear and consistent understanding of the specification and claims, including tile scope to be given such terms, the following definitions are provided.

Cloning vector. A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression vector. A vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

Substantially pure. As used herein means that the desired purified protein is essentially free from contaminating cellular components, said components being associated with the desired protein in nature, as evidenced by a single band following polyacrylamide-sodium dodecyl sulfate gel electrophoresis (SDS-PAGE). Contaminating cellular components may include, but are not limited to, proteinaceous, carbohydrate, or lipid impurities.

The term "substantially pure" is further meant to describe a molecule which is homogeneous by one or more purity or homogeneity characteristics used by those of skill in the art. For example, a substantially pure E2-F1 will show constant and reproducible characteristics within standard experimental deviations for parameters such as the following: molecular weight, chromatographic migration, amino acid composition, amino acid sequence, blocked or unblocked N-terminus, HPLC elution profile, biological activity, and other such parameters. The term, however, is not meant to exclude artificial or synthetic mixtures of the factor with other compounds. In addition, the term is not meant to exclude E2-F1 fusion proteins isolated from a recombinant host.

Recombinant Host. According to the invention, a recombinant host may be any prokaryotic or eukaryotic cell which contains the desired cloned genes on an expression vector or cloning vector. This term is also meant to include those prokaryotic or eukaryotic cells that have been genetically engineered to contain the desired gene(s) in the chromosome or genome of that organism.

Recombinant vector. Any cloning vector or expression vector which contains the desired cloned gene(s).

Host. Any prokaryotic or eukaryotic cell that is the recipient of a replicable expression vector or cloning vector. A "host," as the term is used herein, also includes prokaryotic or eukaryotic cells that can be genetically engineered by well known techniques to contain desired gene(s) on its chromosome or genome. For examples of such hosts, see Sambrook et al., *Molecular Cloning: A Laboratory Manual*, Second Edition, Cold Spring Harbor Laboratory, Cold Spring Harbor, N.Y. (1989).

Promoter. A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter.

Gene. A DNA sequence that contains information needed expressing a polypeptide or protein.

Structural gene. A DNA sequence that is transcribed into messenger RNA (mRNA) that is then translated into a sequence of amino acids characteristic of a specific polypeptide.

Antisense RNA gene/Antisense RNA. In eukaryotes, mRNA is transcribed by RNA polymerase II. However, it is also known that one may construct a gene containing a RNA polymerase II template wherein a RNA sequence is transcribed which has a sequence complementary to that of a specific mRNA but is not normally translated. Such a gene construct is herein termed an "antisense RNA gene" and such a RNA transcript is termed an "antisense RNA." Antisense RNAs are not normally translatable due to the presence of translation stop codons in the antisense RNA sequence.

Antisense oligonucleotide. A DNA or RNA molecule containing a nucleotide sequence which is complementary to that of a specific mRNA. An antisense oligonucleotide binds to the complementary sequence in a specific mRNA and inhibits translation of the mRNA.

Complementary DNA (cDNA). A "complementary DNA," or "cDNA" gene includes recombinant genes synthesized by reverse transcription of mRNA and from which intervening sequences (introns) have been removed.

Expression. Expression is the process by which a polypeptide is produced from a structural gene. The process involves transcription of the gene into mRNA and the translation of such mRNA into polypeptide(s).

Homologous/Nonhomologous. Two nucleic acid molecules or protein fragments are considered to be "homologous" if their nucleotide sequences or amino acid sequences, respectively, share a similarity of greater than 50%. Two nucleic acid molecules or two protein molecules are considered to be "nonhomologous" if their nucleotide sequences or amino acid sequences, respectively, share a similarity of less than 50%.

Ribozyme. A ribozyme is an RNA molecule that contains a catalytic center. The term includes RNA enzymes, self-splicing RNAs, and self-cleaving RNAs.

Fragment. A "fragment" of a molecule such as E2-F1 is meant to refer to any polypeptide subset of that molecule.

Functional Derivative. The term "functional derivatives" is intended to include the "variants," "analogues," or "chemical derivatives" of the molecule. A "variant" of a molecule such as E2-F1 is meant to refer to a naturally occurring molecule substantially similar to either the entire molecule, or a fragment thereof. An "analogue" of a molecule such as E2-F1 is meant to refer to a non-natural molecule substantially similar to either the entire molecule or a fragment thereof.

A molecule is said to be "substantially similar" to another molecule if the sequence of amino acids in both molecules is substantially the same, and if both molecules possess a similar biological activity. Thus, provided that two molecules possess a similar activity, they are considered variants as that term is used herein even if one of the molecules contains additional amino acid residues not found in the other, or if the sequence of amino acid residues is not identical.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in *Remington's Pharmaceutical Sciences* (1980) and will be apparent to those of ordinary skill in the art.

E2-F1. The term "E2-F1" refers to an E2 enzyme having a molecular weight of approximately 18,000 daltons, which is isolated from a fraction of crude reticulocyte lysate that does not absorb to anion exchange resin in neutral pH. The E2-F1 enzyme of the present invention is further characterized by the ability to stimulate protein degradation of non N-end rule substrates and N-α-acetylated substrates.

Immuno-Polymerase Chain Reaction. A method for the detection of antigens using specific antibody-DNA conjugates. According to this method, a linker molecule with bispecific binding affinity for DNA and antibodies is used to attach a DNA molecule specifically to an antigen-antibody complex. As a result, a specific antigen-antibody-DNA conjugate is formed. The attached DNA can be amplified by the polymerase chain reaction (PCR) using appropriate oligonucleotide primers. The presence of specific PCR products demonstrates that DNA molecules are attached specifically to antigen-antibody complexes, thus indicating the presence of antigen. (Sano et al., *Science* 258:120–122 (1992)).

For example, Sano et al., supra, constructed a streptavidin-protein A chimera that possesses specific binding affinity for biotin and immunoglobulin G. This chimera (i.e., the "linker molecule") was used to attach a biotinylated DNA specifically to antigen-monoclonal antibody complexes that had been immobilized on microtiter plate wells. A segment of the attached DNA was subsequently amplified by PCR.

DETAILED DESCRIPTION OF THE INVENTION

This invention is directed to a novel species of ubiquitin-carrier protein, E2-F1, enzymatically active fragments thereof, genetic sequences coding for E2-F1 mRNA, expression vectors containing the genetic sequences, recombinant hosts transformed therewith, and E2-F1 produced by such transformed recombinant host expression. This invention further relates to antibodies directed against E2-F1, as well as the use of E2-F1 antibodies for detection of the presence of E2-F1 in biological samples. The invention further relates to the use of E2-F1 antibodies to inhibit protein degradation in cultured cells. This invention further relates to the use of purified E2-F1 to identify and isolate E3 enzyme. This invention further relates to methods for screening substances for the ability to inhibit E2-F1 enzyme activity. This invention further relates to the therapeutic uses of E2-F1 fragments, E2-F1 antibodies, and E2-F1 inhibitory substances.

I. Isolation of E2-F1 and Preparation of Enzymatically Active Fragments of E2-F1

1. Isolation of E2-F1

The E2-F1 proteins or fragments of this invention may be purified from biological material. Alternatively, E2-F1 may be obtained by expression from recombinant DNA, as described below.

For purposes of the present invention, one method of purification which is illustrative, without being limiting, consists of the following steps.

A first step in the purification of E2-F1 includes the preparation of a reticulocyte lysate. Preferably, the lysate is prepared from the blood of rabbits following phenyl-hydrazine treatment, as described in Hershko et at., *J. Biol. Chem.* 258:8206–8214 (1983), which is fully incorporated by reference.

A second step includes the fractionation of the reticulocyte lysate. Preferably, the lysate is fractionated using ion exchange chromatography on dimethylaminoethyl cellulose DE52.

A third step includes subjecting the unabsorbed fraction of the second step to gel filtration chromatography. Molecular sieve or gel chromatography is a type of partition chromatography in which separation is based on molecular size. Dextran, polyacrylamide, and agarose gels are commonly used for this type of separation. One useful gel for the present invention is Sephadex G-50 (Pharmacia LKB Biotechnology, Inc.). However, other methods, known to those of skill in the art may be used to effectively separate molecules based on size. Elution of E2-F1 can be monitored by testing fractions for the ATP-dependent stimulation of the degradation of substrate proteins. Preferably, the degradation of radioiodinated glyceraldehyde-3-phosphate dehydrogenase is measured as described in Example 1, herein.

A fourth step in a purification protocol for E2-F1 includes pooling fractions of the third step which contain E2-F1 activity, concentrating the sample protein (for example, by ammonium sulfate precipitation), reconstituting the protein in an appropriate buffer (such as, 20 mM Tris-HCl, pH 7.2 and 2 mM dithiothreitol), and further fractionating the sample protein by gel filtration. Preferably, the sample protein is fractionated using Sephadex G-50.

A fifth step in a purification protocol for E2-F1 includes the preparation of a concentrated protein sample by pooling fractions of the fourth step which contain E2-F1 activity, concentrating the sample protein (for example, by ammonium sulfate precipitation), reconstituting the protein in an appropriate buffer (such as, 20 mM Tris-HCl, pH 7.2 and 2 mM dithiothreitol), and dialyzing the sample protein against the reconstitution buffer.

A sixth step in a purification protocol for E2-F1 includes fractionation of the concentrated protein sample of the fifth step using gel filtration chromatography. Preferably, the concentrated protein sample is fractionated using a Fast Protein Liquid Chromatography System with a HiLoad 1.6×60 cm Superdex 75 HR column (Pharmacia).

A preparation of E2-F1 may be further purified by pooling the active fractions from the Superdex gel filtration step, dialyzing against an appropriate buffer (for example, 20 mM Tris-HCl, pH 8.5 and 2 mM dithiothreitol), concentrating the dialyzed sample (for example, by using an Amicon Centricon 10 concentrator), and subjecting the concentrated sample to ion-exchange chromatography. Preferably, ion-exchange chromatography is performed on a Mono-Q column which is connected to a Fast Protein Liquid Chromatography System (Pharmacia LKB Biotechnology, Inc), as described in Example 2, herein. Following elution, fractions are dialyzed against a buffer with a neutral pH (such as 20 mM Tris-HCl, pH 7.2 and 2 mM dithiothreitol), and analyzed for E2-F1 activity, as well as by SDS-PAGE.

It will be appreciated that other purification steps may be substituted for the preferred method described above. Those of skill in the art will be able to devise alternate purification schemes without undue experimentation.

2. Preparation of Enzymatically Active Fragments of E2-F1

The present invention is directed to enzymatically active fragments of E2-F1 enzyme. Such fragments can be obtained by proteolytic cleavage of purified E2-F1 enzyme protein. Useful proteases include trypsin, chymotrypsin, papain, and *Staphylococcus aureus* V8 protease. Conditions for proteolytic cleavage of a protein are well known to those of skill in the art. For example, tryptic digestion may be performed by: 1) dissolving E2-F1 enzyme protein at a concentration between 2 and 10 mg/ml in 0.2M ammonium bicarbonate: 2) adding a freshly prepared solution of trypsin (DCC-treated bovine trypsin) at a concentration of 1 mg/ml in water, giving a final trypsin/E2-F1 enzyme ratio of 1:50; and 3) mixing the sample and incubating at 37° C. for 48 hours (Gooderham, "Peptide Mapping by Thin-Layer Chromatography and High Voltage Electrophoresis," in *Methods in Molecular Biology, Volume 1: Proteins,* J. M. Walker (Ed.), Humana Press, Clinton, N.J., pp.179–192 (1984)).

A proteolytic digest of E2-F1 enzyme can be fractionated by a variety of techniques. For example, a proteolytic digest of E2-F1 enzyme can be fractionated by SDS-PAGE, and the fragments can be recovered from the gel by electroelution (Current Protocols in Molecular Biology, F. M. Ausbel, et at. (Eds.), John Wiley & Sons, New York, pp. 10.5.1–10.5.5 (1987)). Alternatively, high-performance chromatofocusing and hydrophobic-interaction chromatography provide rapid purification with high recovery and minimal denaturation which may occur during SDS-PAGE (Id. at pp. 10.15.1–10.15.9).

E2-F1 enzyme fragments can be routinely analyzed for enzymatic activity using the assays described herein. Thus, E2-F1 enzyme fragments can be tested for the ability to form $^{125}$I-ubiquitin-thiol esters (see Example 3), for the ability to promote the formation of ubiquitin-protein conjugates in the presence of E1 and E3 (see Example 3), and for the ability to stimulate the ubiquitin-dependent degradation of a model protein, such as glyceraldehyde-3-phosphate dehydrogenase (see Example 1).

3. Use of Purified E2-F1 and Its Enzymatically Fragments, and Screening for E2-F1 Inhibitors As described below, purified E2-F1 can be used to generate E2-F1-specific antibodies, which in turn, can be used to detect E2-F1 in a biological sample, and to inhibit E2-F1 enzyme activity in both commercial and clinical settings. Such purified E2-F1 can be isolated from tissues, or can be obtained using recombinant DNA technology, as described below.

Purified E2-F1 can also be used to identify an E3 protein ligase in a biological sample. For example, E3 can be identified in a biological fluid or cellular extract by determining whether the biological sample promotes the formation of ubiquitin-protein conjugates in the presence of E1 and purified E2-F1 (see Example 3). In addition, purified E2-F1 may be used to construct an E2-F1 affinity column, using well known techniques (for example, see *Affinity Chromatography: A Practical Approach*, Dean et al. (Eds.) IRL Press, Washington, D.C. (1985)). Such an E2-F1 affinity column may be used to bind E3 enzyme from a biological sample, as a first step in the isolation and purification of E3 enzyme.

Enzymatically active fragments of E2-F1 can also be used to generate antibodies which are specific for particular domains of the E2-F1 enzyme. In addition, such E2-F1 fragments can be used to inhibit E2-F1-dependent ubiquitination of proteins. For example, the techniques described above can be used to prepare E2-F1 fragments which contain the domain required for forming ubiquitin-E2-F1 thiol ester, but lack the domain that recognizes E3 enzyme. The introduction of such an E2-F1 fragment into a cell would inhibit ubiquitination by decreasing the transfer of ubiquitin to E3. Such E2-F1 fragments can be introduced into cultured cells, or can be administered therapeutically, as described for the commercial and therapeutic uses of E2-F1 antibodies, respectively.

In addition, purified E2-F1 can be used to screen for enzyme inhibitors of the E2-F1 enzyme in vitro. For example, the ability of a substance to inhibit E2-F1 enzyme activity can be determined by observing the inhibition of E2-F1-dependent formation of $^{125}$I-ubiquitin thiol esters in the presence of the test substance, by observing the inhibition of E2-F1-dependent formation of ubiquitin-protein conjugates in the presence of E1, E3 and the test substance, or by testing the ability of purified E2-F1 to stimulate the ubiquitin-dependent degradation of a model protein in the presence of the test substance (see Examples 1 and 3).

Alternatively, cultured cells can be used for the rapid screening of an inhibitor of E2-F1. For example, such rapid screening may be performed by introducing the test substance into cultured cells, wherein the cultured cells are known to degrade at least one identified protein via the E2-F1-dependent pathway. An inhibition of E2-F1-dependant degradation is shown by the accumulation of the identified protein within the cultured cells. Preferably, the cultured cells are myoblasts, myotubes, or dividing cells. Preferably, the identified protein is an N-α-acetylated protein or a non-N end rule protein. More preferably, the identified protein is glyceraldehyde-3-phosphate dehydrogenase, α-crystallin, historic H2A, actin, or tumor suppressor protein, p53.

In addition, purified E2-F1 can be used to identify an inhibitor of E2-F1enzyme activity in muscle cells. For example, muscle tissue can be incubated in vitro in the presence or absence of a potential inhibitor of E2-F1 enzyme activity. The release of a product of muscle protein breakdown in the absence, but not in the presence, of the test substance indicates that the test substance is an E2-F1 inhibitor. Preferred muscle tissue includes a soleus, extensor digitorum longus, diaphragm muscle (or a piece thereof), or muscle fiber bundle teased from a larger muscle. Preferably, such muscle tissue is obtained from an animal subjected to fasting, denervation, febrile infection, or metabolic acidosis, or from a tumor-bearing animal. Preferably, the product of muscle protein breakdown is 3-methylhistidine.

Techniques of cell and organ culture are well known to those of ordinary skill in the art. For example, see *Animal Cell Culture: A Practical Approach*, R. I. Freshney (Ed.), IRL Press, Washington D.C. (1986); Benford et al., "Preparation and Culture of Mammalian Cells," *Biochemical Taxicology: A Practical Approach*, Snell et al. (Eds.), IRL Press, Washington D.C. pp. 57–82 (1987).

Alternatively, an inhibitor of E2-F1 enzyme activity can be identified using intact animals. For example, the test substance can be administered to an animal, and inhibition of E2-F1 enzyme activity can be determined by measuring the excretion of 3-methylhistidine, or by observing a change in the mass of the soleus or extensor digitorum longus muscle. Preferably, the animal has been subjected to fasting, denervation, febrile infection or metabolic acidosis, or the animal is a tumor-bearing animal.

Such inhibitors of E2-F1 enzyme activity can be used commercially (for example, to inhibit degradation of recombinant proteins produced by recombinant hosts), or can be administered therapeutically, as described for the therapeutic uses of E2-F1 antibodies. For example, such inhibitors of E2-F1 enzyme activity can be used to inhibit the loss of muscle mass by interfering with the function of E2-F1 in muscle cells. Alternatively, such inhibitors of E2-F1 enzyme activity can be used therapeutically to inhibit the growth of tumors in an individual by administering the inhibitor under conditions appropriate for the entry of the inhibitor into cancer cells, resulting in an inhibition of cell division of the cancer cells.

II. Isolation and Use of E2-F1 Antibodies

1. Production of E2-F1 Antibodies

The present invention is directed to the production and use of E2-F1-specific antibodies. The term "antibodies" refers to both polyclonal antibodies which are heterogeneous populations, and to monoclonal antibodies which are substantially homogeneous populations. Polyclonal antibodies are derived from the sera of animals immunized with an antigen preparation. An example, of such an antigen preparation is a composition comprising purified E2-F1 and an adjuvant. Examples of adjuvants include Freund's Adjuvant, SAF-1 (Syntex Research, Palo Alto, Calif.), and RAS (Ribi Immunochem Research, Inc., Hamilton, Mont.). Polyclonal antibodies may be isolated and purified from immunized animals using procedures well-known in the art (for example, see Harlow et al., *Antibodies: A Laboratory Manual*, Cold Spring Harbor Press, 1988).

Monoclonal antibodies to specific antigens may be obtained by methods known to those skilled in the art. See, for example, Kohler and Milstein, *Nature* 256:495–497 (1975) and Harlow et al., supra. Such antibodies may be of any immunoglobulin class including IgG, IgM, IgE, IgA, IgD and any subclass thereof. Briefly, monoclonal antibodies can be obtained by injecting mice with a composition comprising purified E2-F1, verifying the presence of antibody production by removing a serum sample, removing the spleen to obtain B-lymphocytes, fusing the B-lymphocytes with myeloma cells to produce hybridomas, cloning the hybridomas, selecting positive clones which produce anti-E2-F1 antibodies, culturing the anti-E2-F1 antibody producing clones, and isolating anti-E2-F1 antibodies from the hybridoma cultures.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for the detection and quantitation of E2-F1 in a biological sample. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopic determinants usually consist of chemically active surface groupings of molecules such as amino acids or sugar side chains and have specific three dimensional structural characteristics as well as specific charge characteristics.

An "antigen" is a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

2. Use of E2-F1 Antibodies to Detect E2-F1 in a Biological Sample

Antibodies directed against E2-F1 can be used to screen biological samples for the presence of E2-F1. The antibodies (or fragments thereof) useful in the present invention are particularly suited for use in in vitro immunoassays to detect the presence of E2-F1 in a biological sample. In such immunoassays, the antibodies (or antibody fragments) may be utilized in liquid phase or, bound to a solid-phase carrier, as described below.

One screening method for determining whether a biological sample contains E2-F1 comprises immunoassays employing radioimmunoassay (RIA) or enzyme-linked immunosorbant assay (ELISA) methodologies. For example, in one form of RIA, the substance under test is mixed with diluted antiserum in the presence of radiolabeled antigen (i.e. E2-F1). In tells method, the concentration of the test substance will be inversely proportional to the amount of labeled antigen bound to the specific antibody and directly related to the amount of free labeled antigen. Other suitable screening methods will be readily apparent to those of skill in the art.

Alternatively, antibodies specific for E2-F1, or a functional derivative, may be delectably labeled with any appropriate marker, for example, a radioisotope, an enzyme, a fluorescent label, a paramagnetic label, or a free radical.

Methods of making and detecting such detectably labeled antibodies or their functional derivatives are well known to those of ordinary skill in the art, and are described in more detail below. Standard reference works setting forth the general principles of immunology include the work of Klein (*Immunology: The Science of Self-Nonself Discrimination*, John Wiley & Sons, New York (1982)); Kennell et al. (*Monoclonal Antibodies and Hybridomas: A New Dimension in Biological Analyses*, Plenum Press, New York (1980)); Campbell ("Monoclonal Antibody Technology," In: *Laboratory Techniques in Biochemistry and Molecular Biology*, Volume 13 (Burdon, R., et al., eds.), Elsevier, Amsterdam (1984)); and Eisen (In: *Microbiology*, 3rd led. (Davis, et al., Harper & Row, Philadelphia (1980)).

Alternatively, the presence of E2-F1 in a biological sample can be detected by treating the biological sample with nitrocellulose, or other solid support which is capable of immobilizing cells, cell particles or soluble proteins. The support may then be washed with suitable buffers followed by treatment with the detectably labeled E2-F1-specific antibody. The solid phase support may then be washed with the buffer a second time to remove unbound antibody. The amount of bound label on said solid support may then be detected by conventional means.

By "solid phase support" is intended any support capable of binding antigen or antibodies. Well-known supports, or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will note many other suitable carriers for binding monoclonal antibody or antigen, or will be able to ascertain the same by use of routine experimentation.

Alternatively, labeled E2-F1-specific antibody/E2-F1 complexes in a sample may be separated from a reaction mixture by contacting the complex with an immobilized antibody or protein which is specific for an immunoglobulin, e.g., *Staphylococcus* protein A, *Staphylococcus* protein G, anti-IgM or anti-IgG antibodies. Such anti-immunoglobulin antibodies may be polyclonal, but are preferably monoclonal. The solid support may then be washed with a suitable buffer to give an immobilized E2-F1/labeled E2-F 1-specific antibody complex. The label may then be detected to give a measure of E2-F1 concentration Of course, the specific concentrations of detectably labeled antibody and E2-F1. the temperature and time of incubation, as well as other assay conditions may be varied, depending on various factors including the concentration of E2-F1 in the sample, the nature of the sample, and the like. The binding activity of a given lot of anti-E2-F1 antibody may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

Detection may be accomplished using any of a variety of immunoassays. For example, by radioactively labeling the E2-F1-specific antibodies or antibody fragments, it is possible to detect E2-F1 through the use of radioimmune assays. A good description of a radioimmune assay may be found in *Laboratory Techniques and Biochemistry in Molecular Biology*, by Work, et al., North Holland Publishing Company, N.Y. (1978), with particular reference to the chapter entitled "An Introduction to Radioimmune Assay and Related Techniques" by Chard, incorporated by reference herein.

The radioactive isotope can be detected by such means as the use of a gamma counter or a scintillation counter or by autoradiography. Isotopes which are particularly useful for the purpose of the present invention are: $^3H$, $^{125}I$, $^{131}I$, $^{35}S$, $^{14}C$, and preferably $^{125}I$.

It is also possible to label the E2-F1-specific antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerytherin, phycocyanin, allophycocyanin, o-phthaldehyde and fluorescamine.

The E2-F1-specific antibody can also be detectably labeled using fluorescence emitting metals such as $^{152}Eu$, or others of the lanthanide series. These metals can be attached to the E2-F1-specific antibody using such metal chelating groups as diethylenetriaminepentaacetic acid or ethylenediaminetetraacetic acid.

The E2-F1-specific antibody also can be detectably labeled by coupling it to a chemiluminescent compound. The presence of the chemiluminescent-tagged E2-F1-specific antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the E2-F1-specific antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Another way in which the E2-F1-specific antibody can be detectably labeled is by linking the same to an enzyme. This enzyme, in turn, when later exposed to its substrate, will react with the substrate in such a manner as to produce a chemical moiety which can be detected, for example, by spectrophotometric, fluorometric or by visual means. Enzymes which can be used to delectably label the E2-F1-specific antibody include, but are not limited to, malate dehydrogenase, staphylococcai nuclease, delta-V-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-VI-phosphate dehydrogenase, glucoamylase and acetylcholinesterase.

Detection of the E2-F1-specific antibody may be accomplished by a scintillation counter, for example, if the detectable label is a radioactive gamma emitter, or by a fluoromelet, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, et al. (*Clin. Chim. Acta* 70:1–31 (1976)) and Schurs, et al. (*Clin. Chim. Acta* 81:1–40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

The binding molecules of the present invention may be adapted for utilization in an immunometric assay, also known as a "two-site" or "sandwich" assay. In a typical immunometric assay, a quantity of unlabeled antibody (or fragment of antibody) is bound to a solid support that is insoluble in the fluid or cellular extract being tested and a quantity of delectably labeled soluble antibody is added to permit detection and/or quantitation of the ternary complex formed between solid-phase antibody, antigen, and labeled antibody.

Typical immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody. This type of forward sandwich assay may be a simple "yes/no" assay to determine whether antigen is present or may be made quantitative by comparing the measure of labeled antibody with that obtained for a standard sample containing known quantities of antigen. Such "two-site" or "sandwich" assays are described by Wide at pages 199–206 of *Radioimmune Assay Method*, edited by Kirkham and Hunter, E. & S. Livingstone, Edinburgh, 1970.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the biological sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

The antibodies of the present invention are also ideally suited for the preparation of an assay kit. Such a kit may comprise a carrier means being compartmentalized to receive in close confinement therewith one or more container means such as vials, tubes and the like, each of said container means comprising the separate elements of the immunoassay.

For example, there may be a container means containing the first antibody immobilized on a solid phase support, and a further container means containing detectably labeled titrating antibodies in solution. Further container means may contain standard solutions comprising serial dilutions of E2-F1 to be detected. The standard solutions of E2-F1 may be used to prepare a standard curve with the concentration of E2-F1 plotted on the abscissa and the detection signal on the ordinate. The results obtained from a sample containing E2-F1 may be interpolated from such a plot to give the concentration of E2-F1 in the biological sample.

Alternatively, antibodies specific for E2-F1, or a functional derivative, may be delectably labeled with DNA by the technique of immuno-polymerase chain reaction (Sano et at., *Science* 258:120–122 (1992)). The polymerase chain reaction (PCR) procedure amplifies specific nucleic acid sequences through a series of manipulations including denaturation, annealing of oligonucleotide primers, and extension of the primers with DNA polymerase (see, for example, Mullis et al., U.S. Pat. No. 4,683,202; Mullis et al., U.S. Pat. No. 4,683,195; Loh et al., *Science* 243:217 (1988)). The steps can be repeated many times, resulting in a large amplification of the number of copies of the original specific sequence. As little as a single copy of a DNA sequence can be amplified to produce hundreds of nanograms of product (Li et al., *Nature* 335:414 (1988)). Other known nucleic acid amplification procedures include transcription-based amplification systems (Kwoh et al., *Proc. Natl. Acad. Sci. USA* 86:1173 (1989); Gingeras et al., WO 88/10315), and the "ligase chain reaction" in which two (or more) oligonucleotides are ligated in the presence of a nucleic acid target having the sequence of the resulting "di-oligonucleotide" thereby amplifying the di-oligonucleotide (Wu et al., *Genomics* 4:560 (1989); Backman et al., EP 320,308; Wallace, EP 336,731; Orgel, WO 89/09835).

For example, the immuno-PCR assay can be carried out by immobilizing various amounts of the test material on the surface of microtiter wells (see Sanzo et al., supra, page 122, footnote 7). The wells are subsequently incubated with E2-F1 monoclonal antibody, washed, and then incubated with biotinylated DNA molecules which have been conjugated to streptavidin-protein chimera (Id.). This chimera binds biotin (via the streptavidin moiety) and the Fc portion of an immunoglobulin G molecule (via the protein A moiety) (Id., at 120; Sanzo et al., *Bio/Technology* 9:1378 (1991)). (Alternatively, a commercially available avidin system may be used instead of the chimera, as described by Ruzicka et al., *Science* 260:698–699 (1993)). The wells are then washed to remove unbound conjugates. Any E2-F1 present in the test material will be bound by the E2-F1 monoclonal antibody, which ill turn, is bound by tile protein A moiety of the biotinylated DNA-streptavidin-protein A conjugate. Then, the DNA sequences are amplified using PCR. Briefly, the microtiter wells are incubated with deoxyribonucleoside triphosphates, oligonucleotide primers, and Taq DNA polymerase (see Sanzo et al., supra, page 122, footnote 11). An automated thermal cycler (such as the PTC-100-96 Thermal Cycler, MJ Research, Inc.) can be used to perform PCR under standard conditions (Id.). The PCR products are then analyzed by agarose gel electrophoresis after staining with ethidium bromide.

Alternatively, tile antibodies of the present invention can be used to detect E2-F1 in tissue sections. In situ detection may be accomplished by removing a histological specimen from a patient, and providing the combination of labeled antibodies of tile present invention to such a specimen. The antibody (or fragment) is preferably provided by applying or by overlaying the labeled antibody (or fragment) to a biological sample. Through the use of such a procedure, it is possible to determine not only the presence of E2-F1, but also the distribution of E2-F1 in the examined tissue. Using the present invention, those of ordinary skill will readily perceive that ally of a wide variety of histological methods (such as staining procedures) can be modified in order to achieve such in situ detection. General techniques of in situ detection are well known to those of ordinary skill and may be found, for example, in Ponder, "Cell Marking Techniques and Their Application," in *Mammalian Development: A Practical Approach*, M. Monk (Ed.), IRL Press, Washington, D.C., pp. 115–138 (1987).

The above-described in vitro and in situ detection methods may be used to assist in the diagnosis or determination of the stage of deterioration in certain pathological conditions. For example, increased ubiquitination is associated with a variety of neurodegenerative diseases. Ubiquitin immunoreactivity has been detected in the Lewy body of Parkinson's disease, the conical Lewy body of Diffuse Lewy body disease, the Pick body of Pick's disease, in Rosenthal fibers of cerebral astrocytomas, and in inclusion bodies of motor neurone disease (Mayer et al., *Acta Biol. Hungar.* 42:21–26 (1991)). Ubiquitin immunoreactivity is found in dystrophic axons of Infantile Neuroaxonal Dystrophy, or Seitelberger's Disease (Moretto et al., *Clin. Neuropathol.* 12:34–37 (1993), in the kuru plaques of Creutzfeldt-Jakob disease (Suenaga et al., *Ann. Neurol.* 28:174–177 (1990)), in anterior horn cells and hypoglossal neurons of Joseph's disease (Suenaga el al., *Acta Neuropathol.* 85:341–344 (1993)), in spinal cord anterior horn cells of amyotrophic lateral sclerosis (Leigh et al., *Brain* 114:775–788 (1991); Mizusawa et al., *J. Neurol. Sci.* 105:14–21 (1991)), associated with preamyloid and cerebral amyloid β deposits in patients with hereditary cerebral hemorrhage with amyloidosis Dutch type (Tagliavini et al., *Acta Neuropathol.* 85:267–271 (1993)), and associated with amyloid deposits in Gerstmann-Sträussler-Scheinker patients (Migheli et al., *Neurosci. Lett.* 121:55–58 (1991)). Ubiquitin immunoreactivity is also associated with neurofibrillary tangles and dystrophic neurites of Alzheimer's disease patients (Mayer et al., supra), as well as in corpora amylacea from normal aged and Alzheimer's disease brains (Cissé et al., *Acta Neuropathol* 85:223–240 (1993)). In addition, ubiquitin immunoreactivity is found in the Mallory bodies of alcoholic liver disease and the cytoplasmic bodies in a rare muscle disease (Lowe et al., *J. Pathol.* 155:9–15 (1988)).

Since ubiquitin immunoreactivity most likely indicates the presence of conjugated rather than free ubiquitin (Mayer et al., supra), the immunohistochemical detection of ubiquitin indicates the increased activity of the ubiquitin pathway. Increased ubiquitination may be the result of an increase in the intracellular concentration of E2-F1 enzymes, among other actors. Thus, the ability to detect such an increase in the presence of E2-F1 in a biological sample (in vitro or in situ) may lead to the further differentiation and diagnosis of the above-identified diseases.

3. Use of E2-F1 Antibodies to Inhibit Protein Degradation

Ubiquitin-dependent proteolysis mediates the degradation of abnormal proteins (for example, see Ciechanover et al., *Cell* 37:57–66 (1984); Seufert et al., *EMBO J.* 9:543–550 (1990)). Therefore, inhibition of ubiquitin-dependent proteolysis should enhance the yield of recombinant proteins which are "abnormal" to eukaryotic recombinant host cells. The E2-F1 antibodies of the present invention can be introduced into cultured recombinant host cells which produce recombinant proteins in order to inhibit E2-F1-mediated protein degradation. For example, liposomes can be used to administer E2-F1 antibodies to the cultured cells. Specifically, cationic lipids can be used to Facilitate the transport of E2-F1 antibodies to the cultured recombinant host cells (for example, see WO91/17424; WO91/16024).

Alternatively, the E2-F1 antibodies of the present invention can be used to decrease the inappropriately enhanced degradation of "normal" proteins, which occurs in certain pathological conditions. For example, infection with "high risk" (i.e. oncogenic) human papilloma virus type 16 or type 18 leads to a decrease in the intracellular level of tumor-suppressor protein, p53, due to a stimulation of ubiquitin-mediated p53 degradation (Scheffner et al., *Cell* 63:1129–1136 (1990)). Human cervical carcinoma cell lines which have been transformed by the "high risk" human papilloma viruses types 16 and 18 are characterized by exceptionally low levels of p53 (Werness et al., *Science* 248:76–79 (1990)). Studies indicate that the stimulation of p53 protein degradation is mediated by the binding of the vital E6 oncoprotein to p53 protein (Scheffner et al., supra). The E6 proteins of the "high risk," but not the "low risk," human papilloma viruses associate with the p53 protein in vitro (Werness et al., supra). Further evidence for a correlation between low p53 levels and oncogenic potential is provided by the observation that the absence of p53 protein predisposes animals to neoplastic disease (Donehower et al, *Nature* 356:215–221 (1992)). As shown herein (see Example 3), E2-F1 is involved in the conjugation and subsequent degradation of p53 and therefore, the inhibition of the E2-F1 enzyme by specific antibodies would lead to an increase in the levels of p53.

Thus, the E2-F1 proteins of the present invention can be administered, as described above, to decrease the ubiquitin-mediated degradation of "normal" proteins, in general. Specifically, E2-F1 antibodies can be used therapeutically to decrease the degradation of p53 protein. Such treatment may be useful, for example, in the treatment of cervical carcinoma.

In general, when providing a patient with E2-F1 antibodies, or fragments thereof, the dosage of administered agent will vary depending upon such factors as the patient's age, weight, height, sex, general medical condition, and previous medical history. Generally, it is desirable to provide the recipient with a dosage of agent which is in the range of from about 1 pg/kg to 10 mg/kg (amount of agent/body weight of patient), although a lower or higher dosage may also be administered.

E2-F1 antibodies, or fragments thereof, may be administered to patients intravenously, intramuscularly, subcutaneously, enterally, or parenterally. When administering E2-F1 antibody by injection, the administration may be by continuous infusion, or by single or multiple boluses.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The antibody of the present invention can be formulated according to known methods to prepare pharmaceutically useful compositions, whereby E2-F1 antibodies, or fragments thereof, are combined in a mixture with a pharmaceutically acceptable carrier vehicle. Suitable vehicles and their formulation are described, for example, in *Remington's Pharmaceutical Sciences* (16th Edition, Osol, A., Ed., Mack, Easton, Pa. 1980)).

Additional pharmaceutical methods may be employed to control the duration of action. Control release preparations can be achieved through the use of polymers to complex or adsorb E2-F1 antibody, or E2-F1 antibody fragment. Controlled delivery can be exercised by selecting appropriate macromolecules (for example, polyesters, polyamino acids, polyvinyl, pyrrolidone, ethylenevinylacetate, methylcellulose, carboxymethylcellulose, or protamine, sulfate), by the concentration of such macromolecules, as well as by methods of incorporation. Another possible method to control the duration of action by controlled release preparations is to incorporate E2-F1 antibody, or fragment thereof, into particles of a polymeric material such as polyesters, polyamino acids, hydrogels, poly(lactic acid) or ethylene vinylacetate copolymers. Alternatively, E2-F1 antibodies or fragments can be entrapped in microcapsules prepared, for example, by coacervation techniques or by interfacial polymerization, for example, hydroxymethylcellulose or gelatinemicrocapsules and poly(methylmethacylate) microcapsules, respectively, or in colloidal drug delivery systems (for example, liposomes, cationic lipids, albumin microspheres, microemulsions, nanoparticles, and nanocapsules) or in macroemulsions. Such techniques are disclosed in *Remington's Pharmaceutical Sciences*, supra.

III. Isolation of DNA Sequences Coding for E2-F1

DNA sequences coding for E2-F1 are derived from a variety of sources. These sources include genomic DNA, cDNA, synthetic DNA, and combinations thereof.

Mammalian E2-F1 genomic DNA can be extracted and purified from any mammalian cell or tissue, by means well known in the art (for example, see Sambrook et al., *Molecular Cloning: A Laboratory Manual*, Second Edition, Cold Spring Harbor Laboratory Press, 1989). The E2-F1 genomic DNA of the invention may or may not include naturally occurring introns. Moreover, such genomic DNA may be obtained in association with the 5' promoter region of the E2-F1 gene sequences and/or with the 3' translational termination region. Further, such genomic DNA may be obtained in association with DNA sequences which encode the 5' nontranslated region of the E2-F1 mRNA and/or with the genetic sequences which encode the 3' nontranslated region. To the extent that a host cell can recognize the transcriptional and/or translational regulatory signals associated with the expression of the mRNA and protein, then the 5' and/or 3' nontranscribed regions of the native gene, and/or, the 5' and/or 3' nontranslated regions of the mRNA, may be retained and employed for transcriptional and translational regulation.

Alternatively, E2-F1 mRNA can be isolated from any cell which expresses E2-F1, and used to produce cDNA by means well known in the art (for example, see Sambrook et al., supra). Preferably, the mRNA preparation used will be enriched in mRNA coding for E2-F1, either naturally, by isolation from cells which produce large amounts of E2-F1, or in vitro, by techniques commonly used to enrich mRNA preparations for specific sequences, such as sucrose gradient centrifugation, or both. E2-F1 mRNA may be obtained from mammalian tissue and cells, or cell lines derived therefrom. Preferably, mammalian cDNA libraries are constructed from rabbit reticulocytes obtained from rabbits which have been treated with phenylhydrazine.

For cloning into a vector, suitable DNA preparations (either genomic or cDNA) are randomly sheared or enzymatically cleaved, respectively, and ligated into appropriate vectors to form a recombinant gene (either genomic or cDNA) library. A DNA sequence encoding E2-F1 may be inserted into a vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Sambrook et al., supra, and are well known in the art.

Libraries containing E2-F1 clones may be screened and the E2-F1 clones identified by any means which specifically selects for E2-F1 DNA such as, for example: 1) by hybridization with an appropriate nucleic acid probe(s) containing a sequence specific for the DNA of this protein; or, 2) by hybridization-selected translational analysis in which native mRNA hybridizes to the clone in question, is translated in vitro, and the translation products are further characterized; or, 3) if the cloned DNA sequences are themselves capable of expressing mRNA, by immunoprecipitation of a translated E2-F1 product produced by the host containing the clone.

Alternatively, a cDNA library can be prepared in λgt11 vector and screened using E2-F1-specific antibodies (Huynh et al., "Constructing and Screening cDNA Libraries in λgt10 and λgt11," in DNA *Cloning: A Practical Approach*, Vol. I, Glover, D. M. (Ed.), IRL Press, Washington, D.C., pp. 49–78 (1985)).

Oligonucleotide probes specific for E2-F1 which can be used to identify clones to this protein can be designed from knowledge of the amino acid sequence of the corresponding E2-F1. For example, the sequence of such oligonucleotide probes can be based upon the amino acid sequence of peptide fragment 20 (i.e., TDQVIQSLIALVNDPQPEHPLR [SEQ ID NO:5]), which is an internal peptide of E2-F1 that was isolated following tryptic digestion, as described in Example 4.

Since the genetic code is degenerate, more than one codon may be used to encode a particular amino acid (Watson, in *Molecular Biology of the Gene Sequence*, 3rd Ed., W. A. Benjamin, Inc., Menlo Park, Calif., pp. 356–357 (1977)). Although a particular amino acid sequence may be encoded by only a single oligonucleotide, frequently the amino acid sequence may be encoded by any of a set of similar oligonucleotides. Importantly, whereas all of the members of this set contain oligonucleotides which are capable of encoding the peptide fragment and thus, potentially contain the same oligonucleotide sequence as the gene sequence which encodes the peptide fragment, only one member of the set contains the nucleotide sequence that is identical to the nucleotide sequence of the gene sequence. Because this member is present within the set, and is capable of hybridizing to DNA even in the presence of other members of this set, it is possible to employ the unfractionated set of oligonucleotides in the same manner in which one would employ a single nucleotide to clone the gene sequence that encodes the peptide.

Using the genetic code, one or more different oligonucleotides can be identified, each of which would be capable of encoding E2-F1 peptides. The probability that a particular oligonucleotide will constitute the actual E2-F1 coding sequence can be estimated by considering abnormal base-pairing relationships and the frequency with which a particular codon is actually used to encode an amino acid in eukaryotic cells. Such "codon usage rules" are disclosed by Lathe et al., *J. Molec. Biol.* 183:1–12 (1985). Using the codon usage rules of Lathe et al., a single oligonucleotide, or set of oligonucleotides, that contains a theoretical "most probable" nucleotide sequence capable of encoding the E2-F1 peptide sequences is identified.

The oligonucleotide, or set of oligonucleotides, containing the theoretical "most probable" sequence capable of identifying the E2-F1 gene sequence fragments is used to identify the sequence of a complementary set of oligonucleotides which is capable of hybridizing to the "most probable" sequence, or set of sequences. An oligonucleotide sequence containing such a complementary sequence can be employed as a probe to identify and isolate E2-F1 gene sequence (for example, see Sambrook et al., supra).

Thus, in summary, the actual identification of E2-F1 peptide sequences, as disclosed in Example 4 herein, permits the identification of a theoretical "most probable" DNA sequence, or set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe to identify and isolate the E2-F1 gene sequence.

The suitable oligonucleotide, or set of oligonucleotides, which is capable of encoding a fragment of the E2-F1 gene (or which is complementary to such an oligonucleotide, or set of oligonucleotides) may be synthesized by means well known in the art (for example, see Sawnbrook et al., supra). Techniques of nucleic acid hybridization and clone identification are disclosed by Sambrook et al., supra. Those members of the above-described gene library which are found to be capable of such hybridization are then analyzed to determine the extent and nature of the E2-F1 encoding sequences which they contain.

To facilitate the detection of the desired E2-F1 coding sequence, the above-described DNA probe is labeled with a detectable group. Such detectable group can be any material having a detectable physical or chemical property. Such materials have been well-developed in the field of nucleic acid hybridization and in general most any label useful in such methods can be applied to the present invention. Particularly useful are radioactive labels including $^{32}P$, $^{3}H$, $^{14}C$, $^{125}I$, or the like. Any radioactive label may be employed which provides for an adequate signal and has sufficient half-life. The DNA probe may be labeled, for example, by nick-translation, by T4 DNA polymerase replacement synthesis, or by random priming, among other methods well known in the an (see Sambrook et al. supra).

Alternatively, DNA probes can be labeled with non-radioactive markers such as biotin, an enzyme, or fluorescent group.

IV. Expressing the Gene Coding for E2-F1

The above-discussed methods are, therefore, capable of identifying DNA sequences which are code for E2-F1 or fragments thereof. In order to further characterize such DNA sequences, and in order to produce the recombinant protein, it is desirable to express the proteins which the DNA sequences encode.

To express E2-F1, transcriptional and translational signals recognizable by an appropriate host are necessary. The cloned E2-F1 DNA sequences, obtained through the methods described above, and preferably in double-stranded form, may be "operably linked" to sequences controlling transcriptional expression in an expression vector, and introduced into a host cell, either prokaryotic or eukaryotic, to produce recombinant E2-F1. Depending upon which strand of the E2-F1 coding sequence is operably linked to the sequences controlling transcriptional expression, it is also possible to express an E2-F1 antisense RNA.

A nucleic acid molecule, such as DNA, is said to be "capable of expressing" a polypeptide if it contains expression control sequences which in turn contain transcriptional regulatory information and such sequences are "operably linked" to the nucleotide sequence which encodes the protein.

Two sequences of a nucleic acid molecule are said to be operably linked when they are linked to each other in a manner which either permits both sequences to be transcribed onto the same RNA transcript, or permits an RNA transcript, begun in one sequence to be extended into the second sequence. Thus, two sequences, such as a promoter sequence and any other "second" sequence of DNA or RNA are operably linked if transcription commencing in the promoter sequence will produce an RNA transcript of the operably linked second sequence. In order to be operably linked it is not necessary that two sequences be immediately adjacent to one another.

Recombinant prokaryotic host cells can express the E2-F1 protein. Alternatively, recombinant E2-F1 can be expressed by such cells as a fusion protein. An especially preferred prokaryotic host is *E. coli*. Preferred strains of *E. coli* include Y1088, Y1089, CSH18, ER1451, and ER1647 (see, for example, *Molecular Biology LabFar*, Brown, T. A., Ed., Academic Press, New York ( 1991 )). An alternative preferred host is *Bacillus subtilus*, including such strains as BRI51, YB886, MI119, MI120, and B170 (see, for example, Hardy, "Bacillus Cloning Methods," in *DNA Cloning: A Practical Approach*, IRL Press, Washington, D.C. (1985)).

Suitable promoters for expression in a prokaryotic host can be repressible, constitutive, or inducible. Examples of suitable prokaryotic promoters include promoters capable of recognizing the T4 polymerases (Malik et al., *J. Biol. Chem.* 263:1174–1181 ( 1984): Rosenberg et al., *Gene* 59:191–200 (1987); Shinedling et al., *J. Molec. Biol.* 195:471–480 (1987); Hu et al., *Gene* 42:21–30 (1986)), T3, Sp6, and T7 (Chamberlin et al., *Nature* 228:227–231 (1970); Bailey et al., *Proc. Natl. Acad. Sci. (U.S.A.)* 80:2814–2818 (1983): Davanloo et al., *Proc. Natl. Acad. Sci.* (U.S.A.) 81:2035–2039 (1984)); the $P_R$ and $P_L$ promoters of bacteriophage lambda (*The Bacteriophage Lambda*, Hershey, A.D., Ed., Cold Spring Harbor Press, Cold Spring Harbor, N.Y. (1973); *Lambda II*, Hendrix, R. W., Ed., Cold Spring Harbor Press, Cold Spring Harbor, N.Y. (1980)); the trp, recA, heat shock, and lacZ promoters of *E. coli;* the α-amylase (Ulmanen et al., *J. Bacteriol.* 162:176–182 (1985)) and the delta-28-specific promoters of *B. subtilis* (Gilman et al., *Gene* 32:11–20 (1984)); the promoters of the bacteriophages of Bacillus (Gryczan, In: *The Molecular Biology of the Bacilli*, Academic Press, Inc., N.Y. (1982)); Streptomyces promoters (Ward et al., *Mol. Gen. Genet.* 203:468–478 (1986)); the int promoter of bacteriophage lambda; the bla promoter of the α-lactamase gene of pBR322, and the CAT promoter of the chloramphenicol acetyl transferase gene of pBR325, etc. Prokaryotic promoters are reviewed by Glick, *J. Ind. Microbiol.* 1 :277–282 ( 1987); Cenatiempo, *Biochimie* 68:505–516 (1986); Watson et al., In: *Molecular Biology of the Gene*, Fourth Edition, Benjamin Cummins, Menlo Park, Calif. (1987): Gottesman, *Ann. Rev. Genet.* 8:415–442 (1984): and Sambrook et al., supra.

Preferably, the present invention encompasses the expression of E2-F1 in eukaryotic cells, and especially mammalian, insect, and yeast cells. Especially preferred eukaryotic hosts are mammalian cells. Mammalian cells provide post-translational modifications to recombinant E2-F1 which include folding and/or phosphorylation. For example, such mammalian host cells include Chinese hamster ovary cells (CHO-K1; ATCC CCL61); rat pituitary cells (GH$_1$; ATCC CCL82); HeLa S3 cells (ATCC CCL2.2): and rat hepatoma cells (H-4-II-E: ATCC CRL1548).

For a mammalian host, the transcriptional and translational regulatory signals may be derived from viral sources, such as adenovirus, bovine papilloma virus, simian virus, or the like, where the regulatory signals are associated with a particular gene which has a high level of expression. In addition, promoters from mammalian expression products, such as actin, collagen, myosin, etc., may be employed. Alternatively, a prokaryotic promoter (such as the bacteriophage T3 RNA polymerase promoter) may be employed, wherein the prokaryotic promoter is regulated by a eukaryotic promoter (for example, see Zhou et al., Mol. Cell. Biol. 10:4529–4537 (1990); Kaufinan et al., Nucl. Acids Res. 19:4485–4490 (1991)). Transcriptional initiation regulatory signals may be selected which allow for repression or activation, so that expression of the genes can be modulated.

The expression of the E2-F1 protein in eukaryotic cells requires the use of eukaryotic regulatory regions. Such regions will, in general, include a promoter region sufficient to direct the initiation of RNA synthesis. Such eukaryotic promoters include the promoter of the mouse metallothionein I gene (Hamer et al., J. Mol. Appl. Gen. 1:273–288 (1982)); the TK promoter of Herpes virus (McKnight, S., Cell 31:355–365 (1982)); the SV40 early promoter (Benoist et al., Nature (London) 290:304–310 (1981)); the Rous sarcoma virus promoter (Gorman et al., supra);the cytomegalovirus promoter (Foecking et al., Gene 45:101 (1980)): and tile yeast gal4 gene promoter (Johnston, et al., Proc. Natl. Acad. Sci. (USA) 79:6971–6975 (1982); Silver, et al., Proc. Natl. Acad. Sci. (USA) 81:5951–5955 (1984)). All of tile above listed references are incorporated by reference herein.

As is widely known, translation of eukaryotic mRNA is initiated at the codon which encodes the first methionine. For this reason, it is preferable to ensure that the linkage between a eukaryotic promoter and a DNA sequence which encodes the E2-F1 protein does not contain any intervening codons which are capable of encoding a methionine (i.e., AUG). The presence of such codons results either in the formation of a fusion protein (if the AUG codon is in the same reading frame as the E2-F1 protein-encoding DNA sequence) or a frame-shift mutation (if the AUG codon is not in the same reading frame as E2-F1 protein encoding sequence).

The E2-F1 protein encoding sequence and an operably linked promoter may be introduced into eukaryotic cells either as a non-replicating DNA (or RNA) molecule, which may either be a linear molecule or, more preferably, a closed covalent circular molecule. Since such molecules are incapable of autonomous replication, the expression E2-F1 protein may occur through the transient expression of the introduced sequence. Alternatively, permanent expression may occur through the integration of the introduced sequence into the host chromosome.

Preferably, the introduced sequence will be incorporated into a plasmid or viral vector capable of autonomous replication in the recipient host. Several possible vector systems are available for this purpose. One class of vectors utilize DNA elements which provide autonomously replicating extrachromosomal plasmids, derived from animal viruses such as bovine papilloma virus, polyoma virus, adenovirus, or SV40 virus. A second class of vectors relies upon the integration of the desired gene sequences into the host chromosome. Additional elements may also be needed for optimal synthesis of mRNA. These elements may include splice signals, as well as transcription promoters, enhancers, and termination signals. The cDNA expression vectors incorporating such elements include those described by Okayama, Mol. Cell. Biol. 3:280 (1983), Sambrook et al., supra, and others.

Strong promoters are the most preferred promoters of tile present invention. Examples of such preferred promoters are those which recognize the T3. SP6 and T7 polymerase promoters; the $P_L$ promoter of bacteriophage lambda: tile recA promoter and the promoter of the mouse metallothionein I gene. The most preferred promoter for expression in prokaryotic cells is one which is capable of recognizing the T7 polymerase promoter. The sequences of such polymerase recognition sequences are disclosed by Watson, et al. (In: Molecular Biology of the Gene, Fourth Edition, Benjamin Cummins, Menlo Park, Calif., (1987)). The most preferred promoter for expression in mammalian cells is SV40 (Gorman, "High Efficiency Gene Transfer into Mammalian cells." in DNA Cloning: A Practical Approach, Volume II, IRL Press, Washington, D.C., pp. 143–190 (1985)).

Having now generally described the invention, the same will be more readily understood through reference to the following Examples which are provided by way of illustration, and are not intended to be limiting of the present invention, unless specified.

EXAMPLE 1

Stimulation of Glyceraldehyde-3-Phosphate Dehydrogenase Degradation by Crude Reticulocyte Fraction 1

1. Preparation of Reticulocyte Fractions

Reticulocyte-rich blood was induced in rabbits by successive injections of phenyl-hydrazine, and reticulocyte lysates were prepared as described (Hershko, A. et al., J. Biol. Chem. 258:8206–8214 (1983)). Lysates were resolved by ion exchange chromatography on dimethylaminoethyl cellulose DE52 (DEAE: Whatman) into unadsorbed material (Fraction 1) and high salt eluate (Fraction 2) as described (Hershko, A. et al., J. Biol. Chem. 258:8206–8214 (1983)).

For degradation experiments, Fraction 2 was not precipitated by $(NH_4)_2SO_4$. Instead, the high salt eluate was dialyzed against a buffer containing 20 mM Tris-HCl, pH 7.2, 5 mM KCl, and 2 mM dithiothreitol (DTT), and concentrated by a Centriflo CF-25 cone (Amicon) to a concentration of approximately 20 mg/ml protein. Fraction 2 was further resolved by $(NH_4)_2SO_4$ into Fraction 2A (0–38% saturation) and Fraction 2B (42–80% saturation) as described (Hershko, A., Proc. Natl. Acad. Sci. USA 76:3107–3110 (1979)). Fraction 2A contains the E3 enzymes while Fraction 2B contains the E1 and E2 enzymes.

2. Degradation of $^{125}$I-Labeled Proteins

For these studies, E1 and E2 were purified from crude reticulocyte Fraction 2 by affinity chromatography on immobilized ubiquitin as described (Hershko, A. et at., J. Biol. Chem. 258:8206–8214 (1983)). Protein substrates were radiolabeled with iodine using the chloramine T method as described (Ferber, S. et al., J. Biol. Chem. 261:3128–3134 (1985)).

Degradation of iodinated proteins was determined by measuring the radioactivity released into trichloroacetic acid-soluble fraction as described (Ferber, S. et al., J. Biol. Chem. 261:3128–3134 (1985)). All assays were carried out in a final volume of 50 μl and contained 35 μl of whole reticulocyte lysate or 200 μg of protein of Fraction 2, 5 μg of ubiquitin and additional fractions as indicated in the description of the specific experiments, below. All reactions were incubated for 2h at 37° C. In all cases, two sets of reaction mixtures were incubated: one set contained ATP and ATP-regenerating system, whereas the other set contained hexokinase and 2-deoxyglucose. Values of ATP-independent degradation did not exceed 20% of energy-dependent breakdown. Results reflect ATP-dependent degradation of substrate proteins.

As shown in Table 1, the addition of crude reticulocyte Fraction 1 to a ubiquitin-supplemented Fraction 2 significantly increases the degradation of rabbit muscle glyceraldehyde-3-phosphate dehydrogenase (GA3PDH). Fraction 1 contains a factor (designated FH) that is necessary for the degradation of N-α-acetylated proteins (Gonen, H. et al., *J. Biol. Chem.* 266:19221–19231 (1991)). This factor, which is a homodimer of approximately 96,000 kDa molecular mass, is required for the degradation of already conjugated proteins. It is not necessary for their ubiquitin tagging. Since rabbit muscle GA3PDH has a free N-terminus (Val; the N-terminal region is 1-Val-Lys-Val-Gly-Val-5[SEQ ID NO: 6]; (Putney, S. D. et al., *Nature* 302:718–721 (1983)); confirmed by direct sequencing of the preparation used in this study), the factor which is necessary for degradation of the dehydrogenase may be different from FH. A direct experiment showed that this is indeed the case. Addition of partially purified FH to ubiquitin-supplemented Fraction 2 had no effect on the degradation of GA3PDH.

Thus, crude reticulocyte Fraction 1 stimulates the degradation of GA3PDH. This dehydrogenase is a homotetramer that is composed of four 35 kDa molecular mass chains with a Val residue in their N-terminal position. Val is a "stabilizing" residue according to the N-end rule in bacteria, yeast, and mammalian cells (Varshavsky, A., *Cell* 69:725–735 (1992)). It was clear, therefore, that this protein is not recognized by E3α and E3β, the two ubiquitin-protein ligases that recognize certain "destabilizing" residues in N-terminal free proteins.

TABLE 1

Effect of Crude Reticulocyte Fraction 1 on the Degradation of Bovine Serum Albumin (BSA), Lysozyme and GA3PDH in Ubiquitin-Supplemented Fraction 2.

| Fraction | $^{125}$I-labeled substrate degradation (%) | | |
|---|---|---|---|
| | BSA | Lysozyme | GA3PDH |
| Whole lysate | 42.4 | 29.7 | 27.8 |
| Fraction 2 | 0.9 | 7.2 | 1.7 |
| Fraction 2 + Ubiquitin | 39.1 | 24.0 | 3.1 |
| Fraction 2 + Ubiquitin + Crude Fraction 1 | 37.4 | 22.6 | 15.9 |

EXAMPLE 2

Purification of E2-F1

In these studies, chromatographic separations were carried out at 4° C. and dialysis of samples at 0° C. The relevant fractions from the different purification steps were subjected to quantitative activity analysis, protein concentration determination (Bradford, M. M., *Anal. Biochem.* 72:248–254 (1976)), and SDS-PAGE (Laemmli, U. K., *Nature* 227:680–685 (1970)). A unit of enzyme is defined as the amount that stimulates the degradation of $^{125}$I-labeled GA3PDH by 1% in a standard protein degradation assay as described above.

In an attempt to remove hemoglobin (which is the major protein in Fraction 1), crude reticulocyte Fraction 1 was resolved by gel filtration chromatography on a Sephadex G-50 column. One hundred milliliters of crude reticulocyte Fraction 1 (121 mg protein/ml) were loaded onto a 4.5×134 cm G-50-150 Sephadex gel filtration column (Pharmacia LKB Biotechnology, Inc.). The proteins were resolved using a buffer that contained 20 mM Tris-HCl, pH 7.2 and 2 mM DTT (Buffer A). Following disposal of the first 550 ml, fractions of 35 ml were collected, and E2 enzyme activity in the fractions was determined in the presence of 30 μl aliquots.

As shown in FIG. 1, most of the hemoglobin was eluted in fractions 4–8 (closed circles indicate protein concentration). In contrast, the stimulatory activity (denoted by the open circles) was recovered in fraction 9–14. This experiment further corroborated the notion that the factor that stimulates the degradation of GA3PDH is different from FH as its native molecular mass is significantly smaller (i.e., it is smaller than hemoglobin).

In order to further characterize the enzyme and remove residual hemoglobin, Sephadex fractions containing the enzyme were concentrated by ammonium sulfate precipitation and further fractionated by gel filtration. fractions 9–14 from the Sephadex G-50 column were pooled, and solid ammonium sulfate was added to 90% saturation and dissolved by gentle stirring on ice. Following a 30 rain incubation on ice, the protein was pelleted by centrifugation at 27,000×g for 15 rain, dissolved in a small volume (2.0 ml) of Buffer A, and dialyzed against the same buffer.

The concentrated protein solution from the previous step was loaded onto a HiLoad 1.6×60 cm Superdex 75 HR column (Pharmacia). Proteins were resolved in a Fast Protein Liquid Chromatography (FPLC) system (Pharmacia) in Buffer A that contained also 50 mM NaCl (Buffer B). Fractions of 2.4 ml were collected. To prevent adsorption of the enzyme, ovalbumin was added to all fractions to a final concentration of 100 μg/ml. Degradation in the different fractions was determined in the presence of 5 μl samples.

Figure 2:
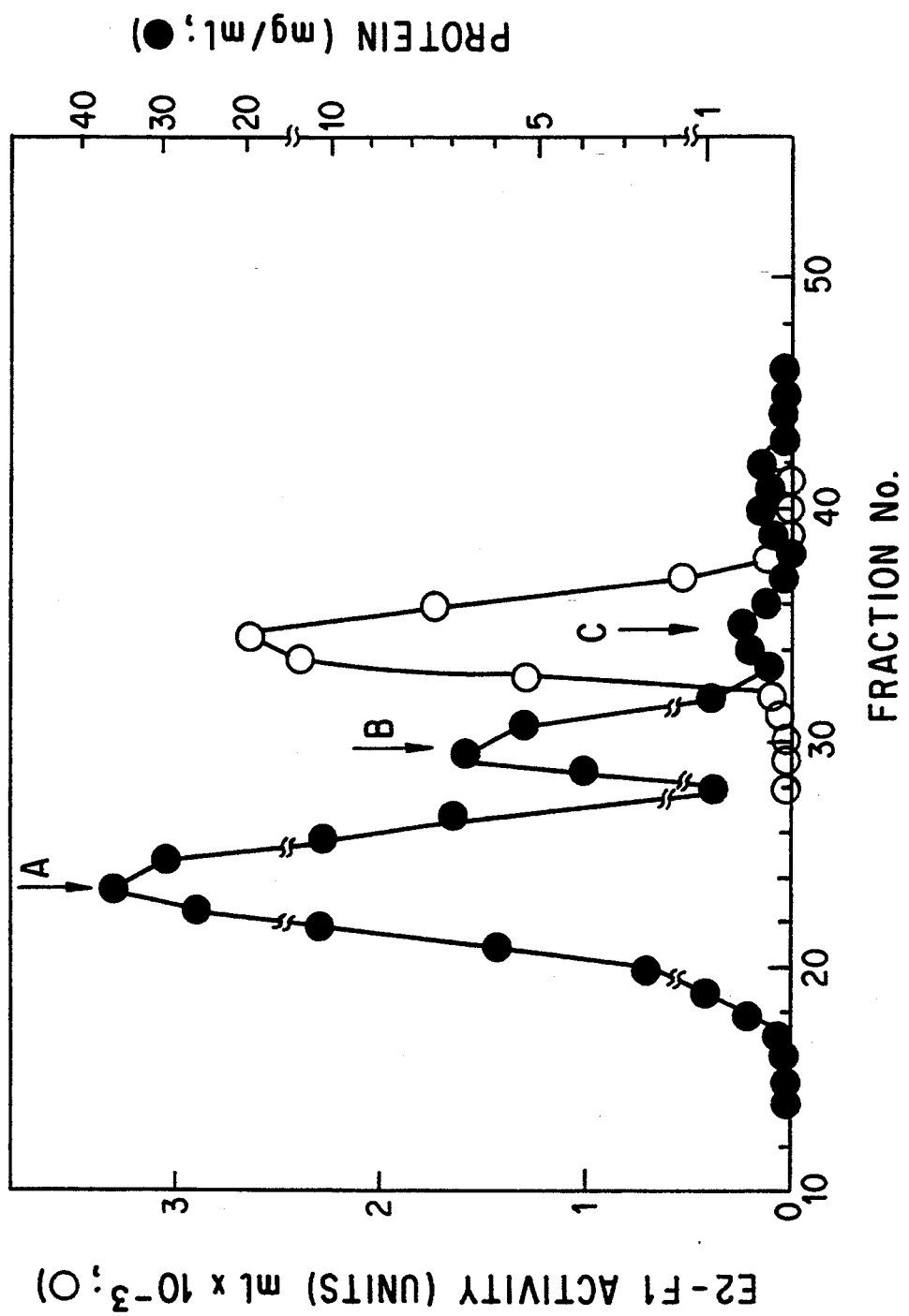
FIG. 2 shows gel filtration chromatography of the Sephadex G-50 resolved E2-F1 on a Superdex 75 column connected to an FPLC system. Closed circles denote protein concentration and open circles denote activity.

The active fractions eluted (33–37) were virtually free from hemoglobin. As shown in FIG. 2, three peaks of protein could be detected, A, B, and C. Peak A contains mostly hemoglobin whereas Peak B contains unidentified proteins. Neither peak contains any E2 enzyme activity. All the activity is resolved with Peak C. Since tile E2 enzyme was present in Fraction 1, the enzyme was designated E2-F1.

At this stage it became clear that the degradation of GA3PDH is mediated by ubiquitin because the protein was not degraded in reaction mixtures that did not contain exogenously added ubiquitin. Since Fraction 1 contains ubiquitin, and since the separation of the crude Fraction over the Sephadex column did not remove ubiquitin completely, it was necessary to demonstrate ubiquitin dependence of GA3PDH degradation at this stage.

Neutralizing antibodies against E1 (Mayer, A. et al., *Science* 244:1480–1483 (1989)) were used to further corroborate the notion that the degradation of the model substrate is mediated by the ubiquitin pathway. The antibody blocked completely the degradation of GA3PDH in crude reticulocyte lysate. Degradation resumed following removal of the antibody and addition of purified E1 (Mayer, A. et al., *Science* 244:1480–1483 (1989)).

Figure 3:
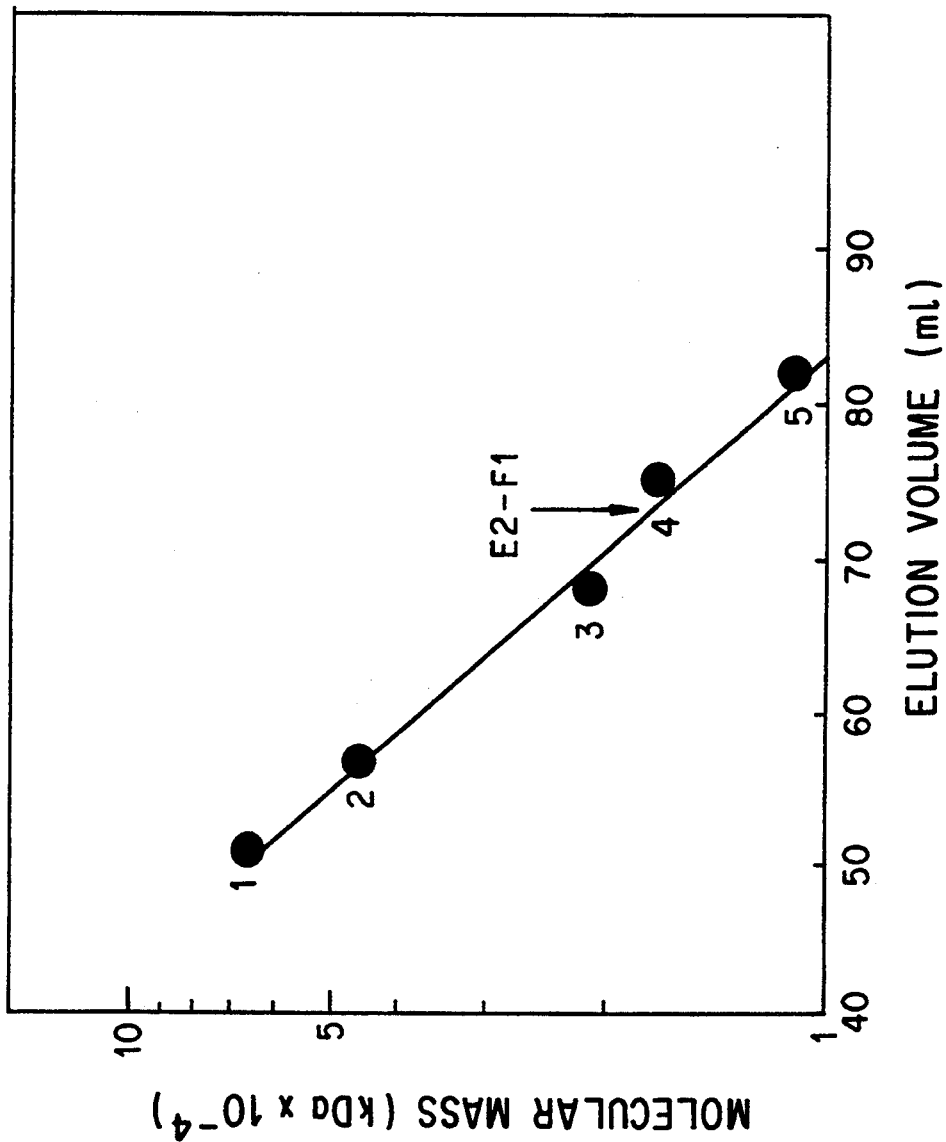
FIG. 3 shows the determination of the molecular mass of E2-F1. Two milligrams each of bovine serum albumin (1), ovalbumin (2), soybean trypsin inhibitor (3), myoglobin (4), and cytochrome C(5), were separated on the Superdex 75 column, and their volume of elution was determined spectrophotometrically at 280 nm. The arrow denotes the point of elution of E2 - F1.

To determine the molecular mass of E2-F1, molecular weight markers were separated on the Superdex 75 column under identical conditions to those that were used to resolve E2-F1. Two milligrams each of bovine serum albumin (1), ovalbumin (2), soybean trypsin inhibitor (3), myoglobin (4), and cytochrome C(5), were separated on the Superdex 75 column, and their volume of elution was determined spectrophotometrically at 280 nm. As shown in FIG. 3, the apparent molecular mass of the enzyme is approximately 18,000 kDa.

The E2-F1-containing fractions from the Superdex 75 gel filtration step were analyzed using sodium dodecyl sulfate polyacrylamide gel electrophoresis (SDS-PAGE). Thirty microliter samples from fractions 31–38 were resolved by SDS-PAGE (12.5% acrylamide) and stained with Coomassie Blue as described below and in Ciechanover, A. et al., Proc. Natl. Acad. Sci USA 77:1365–1368 (1980). The results of SDS-PAGE analysis revealed that bands of three different proteins overlapped with the peak of activity (i.e., fractions 33–37). One protein band had a molecular mass corresponding to that of myoglobin (17,000 kDa), one protein band had a molecular mass of approximately 18,000 kDa, and a third protein band had a molecular mass of approximately 26,000 kDa. Proteins with smaller molecular masses could not be detected in these fractions (except for residual globin chains derived from hemoglobin), thus ruling out the possibility that E2-F1 can be, for example, a homodimer of two 9,000 kDa polypeptide chains.

To further purify E2-F1, fractions 33–37 from the Superdex gel filtration chromatography step were pooled and dialyzed against a buffer that contained 20 mM Tris-HCl, pH 8.5, and 1 mM dithiothreitol (DTT) (Buffer C). The proteins were concentrated to a volume of 0.5 ml and loaded onto a 5×50 mm Mono Q column (Pharmacia) equilibrated in Buffer C and connected to an FPLC system. Following injection of the sample, 6 fractions of 1 ml each were collected before the adsorbed proteins were eluted by a gradient of 0–400 mM KCl in Buffer C. Following collection of 20 fractions of 1 ml, the column was washed with 5 ml of 1 M KCl in Buffer C. To prevent adsorption of the purified enzyme, ovalbumin was added to all fractions to a final concentration of 100 μg/ml. Following elution, all fractions were dialyzed against Buffer A and subjected to activity analysis (i.e., stimulation of degradation of $^{125}$I-GA3PDH, as described above) and SDS-PAGE (Laemmli, U. K., Nature 227:680–685 (1970)).

E2-F1 did not adsorb to the resin even at the mildly alkaline pH 8.5. E2-F1 was recovered in fractions 2–4 in the unadsorbed material with a peak of activity in fraction 3. SDS-PAGE analysis of 25 μl aliquots of these fractions revealed a major protein with a molecular mass of about 18 kDa. Fraction 4 was slightly contaminated with carbonic anhydrase (31 kDa), an abundant protein in reticulocytes. All the other proteins that accompanied E2-F1 in the Superdex 75 gel filtration chromatography were adsorbed to the column, eluted at high salt, and did not contain any activity. Fractions 2–4 were pooled and frozen in small aliquots at −70° C. This preparation was used as a source for purified enzyme for both functional assays and sequence analysis.

TABLE 2

Purification of E2-F1

| Fraction | Volume (ml) | Protein (mg/ml) | Protein (total) | Specific Activity (units/mg protein) | Activity (total) | Purification (x-fold) | Yield (%) |
|---|---|---|---|---|---|---|---|
| Crude Fraction 1 | 100 | 121 | 12,100 | 4.2 | 50,820 | 1.0 | 100 |
| Sephadex G-50 | 210 | 2.5 | 525 | 42.9 | 22,505 | 10.2 | 43 |
| Ammonium sulfate | 2.4 | 203 | 497 | 40.3 | 20,030 | 9.6 | 39 |
| Superdex 75 | 12 | 0.41 | 4.9 | 4138 | 20,280 | 985 | 40 |
| Mono Q | 3 | *0.17 | *0.51 | 13,020 | 6,640 | 3,100 | 13 |

*Fractions eluted from the Mono Q column contained ovalbumin (100 μg/ml). Concentration of protein was estimated by densitometric measurements of the Coomassie Blue staining of increasing amounts of E2-F1 that were compared to the density of bands of known increasing amounts of lysozyme and cytochrome c. Direct measurement of the protein by the Bradford method (Bradford, M.M., Anal. Biochem. 72:248–254 (1976)) following correction for the amount of added ovalbumin yielded similar results.

The purification procedure is summarized in Table 2, and shows that loss of activity occurred mostly in two steps, the Sephadex G-50 gel filtration chromatography and the Mono Q ion exchange chromatography. The reason for these losses is not known. It was possible that other species of E2 or factors necessary for degradation of the test substrate, and that are contained in Fraction 1, were removed during the separation and purification of E2-F1. Such factor(s) could not be found in the remaining fractions from the gel filtration and ion exchange chromatography columns. Also, it was possible that the stimulatory activity that was followed during the resolution, represented as overlap zone between two activities that could not be resolved from one another under the conditions employed.

To test this possibility, samples that were derived from the margins of the peaks of the two gel filtration chromatography steps (left and right margins from the Sephadex and Superdex gel filtration chromatography steps) were added to degradation assays, instead of E2-F1. The stimulation observed in these experiments was additive rather than synergistic. Further support to the notion that the whole activity resides in a single protein is derived from the Mono Q ion exchange chromatography purification step that demonstrates a single protein, and from the functional and structural analyses of the enzyme. In all of the tests E2-F1 appears to be a single protein that requires for its action E1 and E3, both contained in Fraction 2, as described below.

EXAMPLE 3

Functional Analysis of E2-F1

1. Sensitivity to —SH Agents

Since all E2 enzymes contain a functional Cys residue in the active site, the sensitivity of E2-F1 to the -SH blocking agent, N-ethylmaleimide was tested. Fifty units of the enzyme were incubated in the presence of 10 mM of the inhibitor for 10 min at room temperature. The inhibitor was neutralized by the addition of DTT to a final concentration of 5.5 mM, and the activity of the enzyme is stimulating the degradation of $^{125}$I-labeled GA3PDH in ubiquitin-supplemented Fraction 2 was monitored. The enzyme that was incubated in the presence of the inhibitor was completely inactive. An enzyme to which DTT was added prior to the addition of the inhibitor, lost only 28% of its activity compared to a control enzyme or an enzyme preparation that was treated with DTT. Thus. E2-F1 contains a functionally essential —SH group.

2. Formation of $^{125}$I-Ubiquitin-Thiol Ester with E1, E2-F2 and E2-F1

The mechanism of activation of ubiquitin involves formation of a high energy thiol ester intermediate between ubiquitin and E2. The activated ubiquitin moiety is donated to E2 from the ubiquitin activating enzyme, E1 (Ciechanover, A. et al., *J. Biol. Chem.* 257:2537–2542 (1982); Hershko, A. et al., *J. Biol. Chem.* 258:8206–8214 (1983)). To test whether E2-F1 can also generate such a thiol ester, ubiquitin-E1, ubiquitin-E2-F2 (i.e., a conjugate of ubiquitin and E2 from Fraction 2), and ubiquitin-E2-F1 thiol esters were synthesized essentially as described in Ciechanover (Ciechanover. A. et al., *J. Biol. Chem.* 257:2537–2542 (1982)) and Hershko (Hershko, A. et al., *J. Biol. Chem.* 258:8206–8214 (1983)). Briefly, reaction mixtures in a final volume of 25 μl contained: 50 mM Tris-HCl, pH 7.6, 2 mM ATP, 5 mM MgCl$_2$, 0.2 mM DTT, 2.5 units of yeast inorganic pyrophosphatase, 0.5 μg $^{125}$I-labeled ubiquitin (~10$^6$ cpm), 6.0 μg of E1, and 1.2 μg of either E2-F2 or E2-F1 as indicated. When E2 enzymes were added to reaction mixtures that contained E1, the reactions were preincubated for 5 min at 37° C. prior to the addition of the ubiquitin carrier proteins. After the preincubation, 20 μg of unlabeled ubiquitin were added followed by the addition of the E2s. Addition of the unlabeled ubiquitin was necessary to insure that only E1-bound labeled ubiquitin will be transferred to E2. Following incubation for 20 min at 37° C., the samples were divided into two portions. A sample buffer that contains 0.5% SDS but not 2-mercaptoethanol was added to one portion, and a standard sample buffer was added to the other portion. The samples were then resolved via SDS-PAGE (12.5% acrylamide) at 4° C. using a buffer in which the SDS concentration was reduced to 0.5%. Separation was at 5 mA for 12 h. The gels were fixed, dried, and exposed to XAR-5 film (Kodak) as described (Ciechanover, A. et al., *Proc. Natl. Acad. Sci USA* 77:1365–1368 (1980)).

The results of this study demonstrated that fractions 9–14 from the Sephadex G-50 column contain activity that generates a thiol ester in the presence of E1 and that coincides with the activity of E2-F1. The molecular mass of the thiol ester is approximately 25 kDa, corresponding to an adduct composed of a single molecule each of E2-F1 and ubiquitin. The thiol ester disappeared completely following boiling of the samples in the presence of 2-mercaptoethanol. Also, it did not form if E1 was not present. Interestingly, fractions 5–8 contained an additional form of E2 that also generated a thiol ester with E1. This species of E2 was clearly larger than E2-F1 and its function is not known. The fact that the thiol ester it generates with ubiquitin is smaller than the one formed by E2-F1 suggests that in its native form, this E2 can be a multitactic protein since separation of the thiol ester in a buffer that contains SDS separates the monomers from one another.

The ability of the purified E2-F1 to generate a thiol ester with ubiquitin was examined. Ubiquitin E2-F1 thiol esters were generated using Mono Q purified E2-F1, and the results were analyzed using SDS-PAGE, as described above. The results of this study demonstrated that Mono Q-purified E2-F1 generates a thiol ester with ubiquitin. Again, the molecular mass of the thiol ester corresponds to a single adduct between ubiquitin and E2, and the reaction is dependent on the presence of E1.

Moreover, the ester is sensitive to 2-mercaptoethanol; the ester was not observed in samples which had been treated with 2-mercaptoethanol and boiled before application to the gel. Also, the ester was not formed when excess unlabeled ubiquitin was added simultaneously with the labeled ubiquitin and E1, suggesting that only the E1-bound ubiquitin is donated to E2. The thiol esters generated with E2-F2 represented only the small molecular weight species of E2 enzymes that bound to the ubiquitin column. The larger species were removed by an additional gel filtration step of the affinity column resolved E2s.

Several species of E2 enzymes generate mono-ubiquitin conjugates with certain protein substrates. Other species of E2s, along with E3 enzymes, mediate the generation of multiply ubiquitinated proteins that are destined for degradation. To examine the role of E2-F1 in the conjugation process, ubiquitin protein conjugates were generated essentially as described in Gonen (Gonen, H. et al., *J. Biol. Chem.* 266:19221–19231 (1991)). Briefly, the reaction mixture contained in a final volume of 25 μl: 50 mM Tris-HCl, pH 7.6, 5 mM MgCl$_2$, 2 mM DTT, 2 mM ATP, 1.0 μg $^{125}$I-labeled ubiquitin (~150,000 cpm), and Fraction 2 (100 μg), E1 (1.25 μg), E2 enzymes (0.25 μg), and Fraction 2A (80 μg), as indicated. Following incubation of 20 min at 37° C., the reactions were resolved via SDS-PAGE (12.5% acrylamide) and the gels were fixed, dried, and exposed as described (Ciechanover, A. et al., *Proc. Natl. Acad. Sci USA* 77:1365–1368 (1980)).

The results of this study indicate that E2-F1 generates high molecular mass conjugates only in the presence of E1 and E3. Moreover, the addition of 0.2 mM PPi and 2 mM AMP, which blocks the E1-dependent activation of ubiquitin, also inhibits conjugate formation. Quantitative analysis reveals that E2-F1 is at least 5-fold more "efficient" than its Fraction 2 counterpart(s) since it generates 6-fold more conjugates when equal amounts of the two enzymes were used. This "efficiency" probably reflects availability of appropriate substrates in crude Fraction A rather than higher affinity or smaller Km for the same substrates. Probably, non "N-end rule" substrates that are conjugated/degraded via the E2-F1/E3 pathway are more abundant than "N-end rule" substrates degraded via the E2-F1/E3α/E3β pathway.

3. Additional Substrates of E2-F1

In addition to GA3PDH, bovine serum albumin, and lysozyme, E2-F1 stimulates the degradation of actin, histone H2A, and α-crystallin, three N-α-acetylated proteins in a reconstituted system. Furthermore, it increases dramatically the conjugation of ubiquitin to histone H2A in a reconstituted system. Thus, it seems that the new E2 plays an important role in targeting non "N-end rule" substrates for degradation. Moreover, E2-F1 is involved in the conjugation and degradation of tumor suppressor protein, p53, in vitro. Species of p53 that are stable in vivo are not recognized by E2-F1 in vitro, indicating that E2-F1 fulfills a similar function in intact cells in vivo.

EXAMPLE 4

Sequence Analysis of Purified E2-F1

Approximately 400 pmoles (7.2 μg) of E2-F1, derived from the Mono-Q purification step, were blotted from a 10-20% SDS-polyacrylamide gel (Enprotech, Natick, Mass.) onto a Trans-Blot Transfer PVDF membrane (Bio Rad, Richmond, Calif.) using the protocol of Matsudaira (Matsudaira, P., *J. Biol. Chem.* 262:10035–10038 (1987)) and sequence analysis was attempted in an N-terminal fashion. Once failure to derive sequence information suggested N-terminal blockage, in situ cyanogen bromide (CNBr) digestion was performed in the following manner. The PVDF pieces were removed from the sequencer and immersed in 100 μl 3 % CNBr and 70% formic acid. The reaction was incubated overnight in the dark and the pieces were reloaded onto the sequencer with a Polybrene filter overlay to which CNBr supernatant was applied. Automated sequencing was reinitiated.

In order to obtain internal sequence information, peptide fragments were obtained as following. 18 μg (approximately 1,000 pmoles) of E2-F1 were blotted onto PVDF membrane as described above. An in situ trypsinolysis was performed as described by Fernandez and colleagues (Fernandez, J. et al., *Anal. Biochem.* 201:255–264 (1992)). Tryptic peptides released from the PVDF membrane were separated by RP-HPLC using a Brownlee RP-300 Aquapore C8 column (ABI, Foster City. Calif.) developed by a 0.1–70% acetonitrile gradient in 0.085% trifluoroacetic acid (TFA) over a period of 120 min. The tryptic peptides were hand collected and selected peptides were subjected to N-terminal sequence analysis.

Automated Edman degradation chemistry was used for amino acid sequence analysis. An Applied Biosystems, Inc., Model 470A gas phase sequencer (Foster City, Calif.) was employed for the degradations (Hunkapiller, M. W. et al., *Methods Enzymol.* 91:399–413 (1983)) using the standard sequencer cycle 03RPTH. The respective PTH-aa derivatives were identified by RP-HPLC analysis in an on-line fashion employing an Applied Biosystems, Inc., Model 120A PTH Analyzer fitted with a Brownlee 2.1 mm I.D. PTH-C18 column.

Similarities between the obtained sequences and known protein sequences were investigated through computer based searches of the NBRF (National Biomedical Research Foundation) protein sequence databases, Genpept, SwissProt, PIR, SPUpdate, tfd, palu, and GPUpdate protein databases (Devereux, J. et al., *Nucl. Acid Res.* 12:387–395 (1984); Sidman, K. E. et al., *Nucl. Acid Res.* 16:1869–1871 (1980); Bilofsky, H. S. et al., *Nucl. Acid Res.* 16:1861–1864 (1988)), and NCBI (National Center for Biotechnology Information), using the BLAST Network Service.

Two peptides derived from the cyanogen bromide cleavage were analyzed, yielding the following sequences: XXFRNIQVDXANLLTXQGLIVPDNP (major peptide) [SEQ ID NO: 1] and XXLE(H)PLKAXTXX-FY(N)IXV (minor peptide) [SEQ ID NO: 2]. Comparison of the sequences with several protein sequence databases failed to yield any significant homologies. Tryptic hydrolysis generated several internal fragments. Three of these fragments (Pickart, C. M. et al., *J. Biol. Chem.* 260:1573–1581 (1985), Brown, J. L. et al., *J. Biol. Chem.* 251:1009–1014 (1976) and Girod. P. A. et al., *J. Biol. Chem.* 268:955–960 (1993)) were subjected to Edman degradation and their sequences revealed homologies to several known species of E2 enzymes. The sequences of the three fragments are: 1) IYHPNIDEK (Fragment 7; [SEQ ID NO:3]); 2) IEINFPA-EYPFKPPK (Fragment 17; [SEQ ID NO:4]); and 3) TDQVIQSLIALVNDPQPEHPLR (Fragment 20; [SEQ ID NO:5]).

FIG. 4 shows the amino acid sequence comparison between the three internal fragments of E2-F1 from rabbit reticulocytes (R Relic) and several members of the ubiquitin-carrier protein family. Sequences of other proteins used in the analysis were obtained from the following reports: 1) the 14 kDa E2 from rabbit muscle (E2-14 R Musc; Wing, S. S. et al., *J. Biol. Chem.* 26 7:6495–6501 (1992)): 2) E2 UBC1 from the yeast *Saccharomyces cerevisiae* (UBC1 Sc; Seufert, W. et al., *EMBO J.* 9:4535–4541 (1990)); 3) E2 UBC2/RAD6 from the yeast *Saccharomyces cerevisiae* (UBC2/RAD6 Sc: Jentsch et al., *Nature* 329:13 1–134 (1987)); 4) E2 UBC3/cdc34 from the yeast *Saccharomyces cerevisiae* (UBC3/cdc34 Sc; Goebl, M. et al., *Science* 241:1331–1335 (1988)); 5) the E2 proteins UBC4 and UBC5 from the yeast *Saccharomyces cerevisiae* (UBC4 Sc and UBC5 Sc; Seufert, W. et at., *EMBO J.* 9:543–550 (1990)): 6) E2 UBCD1 from the fruit fly *Drosophila melanogaster* (UBCD1 Dm; Treier, M. et al., *EMBO J.* 11:367–372 (1992)); 7) E2 from the African Swine Fever Virus (E2, ASFV; Hingamp, P. M. et al., *EMBO J.* 11:361–366 (1992)); 8) the 23 kDa E2 from the wheat germ *Triticum vulgare* (E2-23 Tv; Sullivan, M. L. et al., *Proc. Natl. Acad. Sci. USA* 86:9861–9865 (1989)); and 9) the 16 kDa E2 from the high plant *Arabidopsis thaliana* (E2-16 At: Sullivan. M. L. et al., *J. Biol. Chem.* 266:23878–23885 (1991)). Identical amino acid residues are indicated by shaded boxes. Numbers flanking the sequences indicate positions of residues along the polypeptide chain, whereas numbers in brackets indicate homology in percentage.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application was specifically and individually indicated to be incorporated by reference in their entirety.

---

What is claimed is:

1. Isolated E2-F1 enzyme which is substantially pure, wherein said E2-F1 enzyme does not bind to anion exchange resin in neutral pH, and comprises the amino acid sequences of SEQ ID NO:3, SEQ ID NO:4 and SEQ ID NO:5 and wherein said E2-F1 enzyme is capable of stimulating protein degradation of non N-end rule substrates and N-α-acetylated substrates.

* * * * *